(12) United States Patent
Soerensen et al.

(10) Patent No.: US 10,213,559 B2
(45) Date of Patent: Feb. 26, 2019

(54) DRUG DELIVERY DEVICE WITH BRAKE MECHANISM

(71) Applicant: Novo Nordisk A/S, Bagsvaerd (DK)

(72) Inventors: Morten Soerensen, Ballerup (DK); Bo Kvolsbjerg, Helsingoer (DK); Kalle Holck Madsen, Copenhagen N (DK); Christian Plambech, Soeborg (DK); Jesper Peter Windum, Hilleroed (DK)

(73) Assignee: Novo Nordisk A/S, Bagsværd (DK)

( * ) Notice: Subject to any disclaimer, the term of this patent is extended or adjusted under 35 U.S.C. 154(b) by 274 days.

(21) Appl. No.: 15/028,867

(22) PCT Filed: Oct. 14, 2014

(86) PCT No.: PCT/EP2014/072001
§ 371 (c)(1),
(2) Date: Apr. 12, 2016

(87) PCT Pub. No.: WO2015/055642
PCT Pub. Date: Apr. 23, 2015

(65) Prior Publication Data
US 2016/0235924 A1    Aug. 18, 2016

Related U.S. Application Data

(60) Provisional application No. 61/902,383, filed on Nov. 11, 2013.

(30) Foreign Application Priority Data

Oct. 16, 2013  (EP) ..................................... 13188955

(51) Int. Cl.
*A61M 5/315* (2006.01)
*A61M 5/24* (2006.01)
(Continued)

(52) U.S. Cl.
CPC .......... *A61M 5/31563* (2013.01); *A61M 5/20* (2013.01); *A61M 5/2033* (2013.01);
(Continued)

(58) Field of Classification Search
CPC .......... A61M 5/31563; A61M 5/31528; A61M 5/31551; A61M 5/2033; A61M 5/31583;
(Continued)

(56) References Cited

U.S. PATENT DOCUMENTS 5,480,387 A    1/1996 Gabriel et al.
8,398,593 B2   3/2013 Eich et al.
(Continued)

FOREIGN PATENT DOCUMENTS

EP    0246158 A1   11/1987
EP    2474332 A1   7/2012
(Continued)

*Primary Examiner* — Amber Stiles
(74) *Attorney, Agent, or Firm* — Wesley Nicolas

(57) ABSTRACT

A drug delivery device (1) comprises a housing and an expelling assembly adapted to expel a dose of drug from a cartridge (380). The expelling assembly comprises a drive spring (135) which in an energized state is adapted to drive the expelling assembly, a rotating component (550,650) adapted to rotate relative to an axis of rotation during expelling of a dose of drug, and user actuated release means (191, 190) for releasing the drive spring to thereby expel a dose of drug. The device is provided with a brake element (575, 675) being moveable in a plane generally perpendicular to the axis of rotation, the brake element being adapted to engage the rotating component such that during rotation thereof the brake element is moved back and forth, whereby the brake element provides a braking action on the rotating component.

28 Claims, 15 Drawing Sheets

(51) Int. Cl.
*A61M 5/20* (2006.01)
*A61M 5/31* (2006.01)

(52) U.S. Cl.
CPC .......... *A61M 5/24* (2013.01); *A61M 5/31501* (2013.01); *A61M 5/31528* (2013.01); *A61M 5/31551* (2013.01); *A61M 5/31553* (2013.01); *A61M 5/31583* (2013.01); *A61M 2005/2411* (2013.01); *A61M 2005/3143* (2013.01)

(58) Field of Classification Search
CPC ...... A61M 5/20; A61M 5/31553; A61M 5/24; A61M 5/31501; A61M 2005/2411; A61M 2005/3143
See application file for complete search history.

(56) References Cited

U.S. PATENT DOCUMENTS

| | | |
|---|---|---|
| 2004/0215153 A1 | 10/2004 | Graf et al. |
| 2011/0054412 A1 | 3/2011 | Eich et al. |
| 2011/0077595 A1* | 3/2011 | Eich .................. A61M 5/31501 604/135 |
| 2017/0340829 A1 | 11/2017 | Cronenberg et al. |

FOREIGN PATENT DOCUMENTS

| | | |
|---|---|---|
| GB | 2443390 A | 5/2008 |
| JP | 2013512070 A | 4/2013 |

* cited by examiner

DRUG DELIVERY DEVICE WITH BRAKE MECHANISM

CROSS-REFERENCE TO RELATED APPLICATIONS

This application is a 35 U.S.C. § 371 National Stage application of International Application PCT/EP2014/072001 (published as WO 2015/055642), filed Oct. 14, 2014, which claims priority to European Patent Application 13188955.2, filed Oct. 16, 2013; this application claims priority under 35 U.S.C. § 119 to U.S. Provisional Application 61/902,383; filed Nov. 11, 2013.

The present invention generally relates to drug delivery devices adapted to hold a drug filled cartridge and expel a dose therefrom.

BACKGROUND OF THE INVENTION

In the disclosure of the present invention reference is mostly made to the treatment of diabetes, however, this is only an exemplary use of the present invention.

The most common type of drug delivery device adapted to deliver a given drug subcutaneously is in the form of a pen-formed drug delivery device adapted to expel a desired amount of drug from a loaded cartridge by moving a cartridge piston in a distal direction to thereby expel drug via an attached subcutaneous needle. The means for moving the piston is typically in the form of a piston rod driven distally by an expelling mechanism. The device may be supplied as a "pre-filled" disposable device in which the drug-filled cartridge cannot be exchanged and the device is to be discarded when the cartridge has been emptied, or as a "durable" reusable device in which a cartridge can be inserted and subsequently removed by the user in order to allow a new cartridge to be inserted. A further distinction can be made between "manual" drug delivery devices in which the energy for driving expelling mechanism is supplied directly by the user during injection, and "automatic" drug delivery devices in which an energy source is released by the user to thereby drive the expelling mechanism. The energy source may be in the form of a spring which is strained by the user during setting of a desired dose. The spring-driven devices may be pre-filled as the FlexTouch® from Novo Nordisk or durable as the ServoPen® from Ypsomed. Alternatively, a pre-filled device may be provided with a pre-strained spring adapted to expel the full content of the cartridge, the individual doses being set by the user. The present invention addresses issues related to spring-driven drug delivery devices of the durable type, which may be either of the traditional type with a detachable cartridge holder or be front-loaded, as well as drug delivery devices of the prefilled type.

During normal operation the drug product has to flow through a narrow needle during the dispensing operation, the viscosity of the drug thereby opposing the force of the piston drive element, e.g. a piston rod, so that the drive element and the additional components of the expelling mechanism remain at a relatively low speed level during expelling of a dose of drug. The relatively low speed level results in relatively low impulses or impacts when one moving part or component hits another part or component in the injection device, which has a positive effect on the service life of the device. However, this is only true if a drug cartridge has been inserted in the device. If a user initiates a drug dispensing operation without an inserted cartridge there will be no damping effect. This can lead to very high acceleration values for the components in the expelling mechanism of the device, especially for rotating components, causing high-energy impacts when components make contact with one another, this potentially having a negative effect on the service life of the device. As a result, the device may be damaged so that it can no longer be used to administer drug or, even worse, be damaged so that an incorrect amount of drug is expelled. Increasing the dimensions accordingly, e.g. to absorb or counter impacts on or between moving parts, would typically increase the size of the device and/or result in additional costs.

The above-described situation may also arise when a new cartridge is inserted without the piston drive element contacting the piston. This will be the case if, for example, the drive element is pushed too far back during the process of changing the cartridge or if a partially full cartridge is inserted, or drug has leaked out of the cartridge through an attached needle. In these situations, too, extreme acceleration values can occur during the idle stroke of the drive element, e.g. the portion of the stroke performed by the drive element until it makes contact with the cartridge piston. Further, if a needle is not mounted on the cartridge in such a situation, the drug in the cartridge is compressed due to the impact of the drive element, this potentially causing damage, e.g. fracture, of an inserted glass cartridge. Correspondingly, a prefilled device may be supplied to a user with a gap between the piston and the drive element.

The above issue has been addressed in US 2011/054412 and US 2011/0077595 disclosing a pen-type drug delivery device with a brake mechanism in which a brake element is moved back and forth during rotational movement of the expelling mechanism, this resulting in mechanical energy being dissipated as heat and thereby a braking action on the expelling mechanism. GB 2 443 390 discloses an automatic type pen device with a manual user-actuated brake element. US 2004/0215153 and U.S. Pat. No. 5,480,387 disclose pen-type drug delivery devices with brake elements in the form of static friction elements.

Having regard to the above, it is an object of the present invention to provide a drug delivery device with a brake mechanism which is compact, effective and reliable. The brake arrangement should be cost-effective and allow a high degree of freedom of design for the device and the incorporated expelling mechanism.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device comprising or being adapted to receive a cartridge is provided, the cartridge comprising a cylindrical body portion, an axially displaceable piston, and a distal outlet portion. The cylindrical body portion may have any suitable cross-sectional configuration, e.g. circular, oval or triangular. The drug delivery device comprises a housing and an expelling assembly adapted to axially move the piston of a cartridge to thereby expel a dose of drug. The expelling assembly comprises a drive spring which in an energized state is adapted to drive the expelling assembly, a rotating component adapted to rotate relative to an axis of rotation during expelling of a dose of drug, and user actuated release means for releasing the drive spring to thereby expel a dose of drug. The device further comprises a brake element being moveable in a plane perpendicular to the axis of rotation, the brake element being adapted to engage the rotating component such that during rotation thereof the brake element is moved back and forth by the rotating component, whereby the brake element provides a braking action on the rotating component.

By arranging the brake element to move radially in the perpendicular plane a brake for a drug delivery device is provided which can be both compact and allow a high degree of freedom of design as exemplified below. It should be noted that the term "perpendicular" is not to be construed literally as the specific design of a brake arrangement may allow the brake element (or more brake elements) to move in a plane which may be inclined somewhat compared to strictly perpendicular, however, still would be considered to be generally perpendicular by the skilled person. An example of a specific design which would allow the orientation of the plane of movement for the brake element to deviate from strictly perpendicular will be given below.

The one or more brake elements may be freely moveable within their boundaries, i.e. not being connected to other structures, e.g. by a hinge.

In an exemplary embodiment the brake element has a generally oval-shaped form, whereas in another exemplary embodiment the drug delivery device comprises a plurality of brake elements.

The one or more brake elements may be arranged non-rotational relative to the housing. For example, the drug delivery device may comprise a non-rotational guide structure adapted to engage the one or more brake elements to thereby guide the one or more brake elements corresponding to the back and forth movement. The guide structure may be formed integrally with a portion of the housing.

The back and forth movement for the individual brake element may be radial, e.g. oriented towards the centre of the generally cylindrical device, or it may deviate therefrom. The movement may be linear or non-linear, e.g. curved. In order to provide the back and forth movement of the brake element(s) the rotating component may comprise an engagement structure for engaging the one or more brake elements during rotation, the engagement structure comprising one or more radially oriented serrated surface structures.

In an exemplary embodiment the brake element is in the form of an oval-like ring and the engagement structure is in the form of a single circumferential array of in- or outwardly directed pointed tooth-like brake structures providing a serrated surface structure. The brake ring comprises a pair of opposed engagement structures adapted to engage, one at a time, opposed brake structures as the rotating element rotates, this resulting in the brake ring being "kicked" radially back and forth. To control the movement the brake ring is provided with a guide structure engaging the non-rotational guide structure of the device. In this embodiment the guide structures as well as the brake ring will typically be arranged perpendicularly to the axis of rotation. Correspondingly, the brake structures will typically also be arranged on a perpendicular surface.

In an alternative exemplary embodiment the device comprises a plurality of circumferentially arranged brake elements and the engagement structure is in the form of two circumferential arrays of in-respectively outwardly directed pointed tooth-like brake structures providing two serrated surface structure opposing each other. The brake elements are arranged corresponding to the gap between the two arrays and are "kicked" back and forth between the two opposed structures, the brake elements being guided in non-rotational guide structures. As in the above embodiments the different structures may be oriented generally perpendicularly to the axis of rotation, however, as the individual brake elements are not moved across the axis of rotation, the rotational and non-rotational surfaces carrying the brake—respectively guide structures could have a mating conical configuration with the brake elements arranged there between.

In some of the above-described exemplary embodiments the one or more brake elements are arranged non-rotational relative to the housing, however, in alternative embodiments the brake element(s) may be arranged non-rotational relative to the rotating component, i.e. rotating together with the rotating component relative to the housing. A guide structure may be formed integrally with the rotating component and be adapted to engage the brake element(s) to thereby guide the brake element(s) corresponding to the back and forth movement, e.g. radially. A non-rotational engagement structure for engaging the brake element(s) during rotation and comprising one or more radially oriented serrated surface structures may be provided, e.g. formed integrally with a portion of the housing.

In the above-described embodiments the expelling assembly may comprise a piston rod adapted to engage and axially displace a piston in a loaded cartridge in a distal direction to thereby expel a dose of drug from the cartridge, the rotating component being in the form of a drive member adapted to be rotated by the strained drive spring to thereby move the piston rod in the distal direction.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. When it is defined that members are mounted axially free to each other it generally indicates that they can be moved relative to each other, typically between defined stop positions whereas when it is defined that members are mounted rotationally free to each other it generally indicates that they can be rotated relative to each other either freely or between defined stop positions. The terms "assembly" and "subassembly" do not imply that the described components necessarily can be assembled to provide a unitary or functional assembly or subassembly during a given assembly procedure but is merely used to describe components grouped together as being functionally more closely related.

Figure 1A:
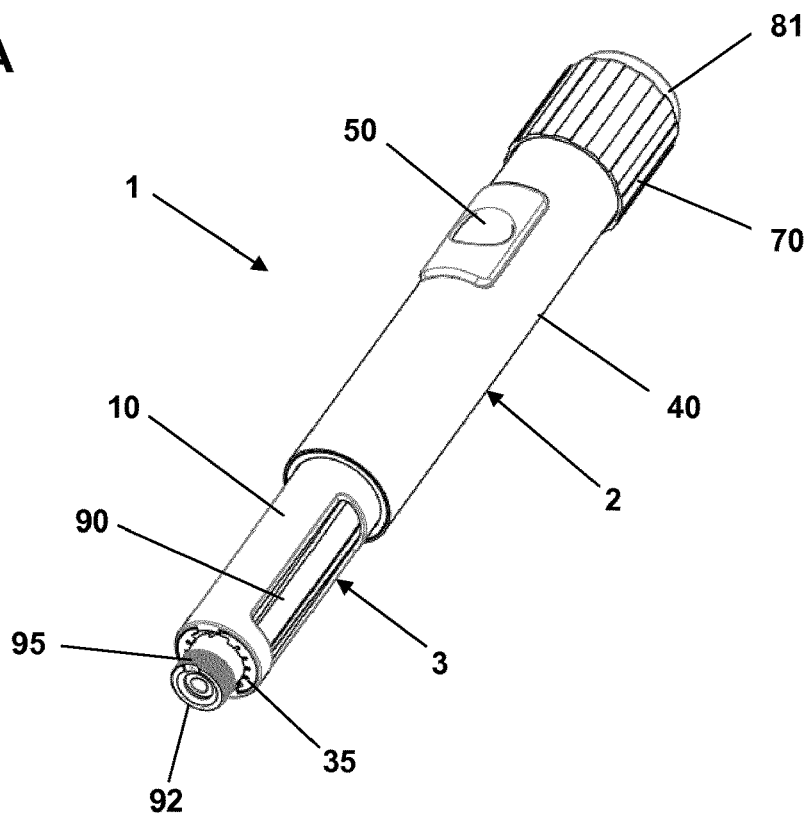
FIGS. 1A and 1B show a front-loaded drug delivery device with respectively without a drug cartridge mounted.
Figure 1B:
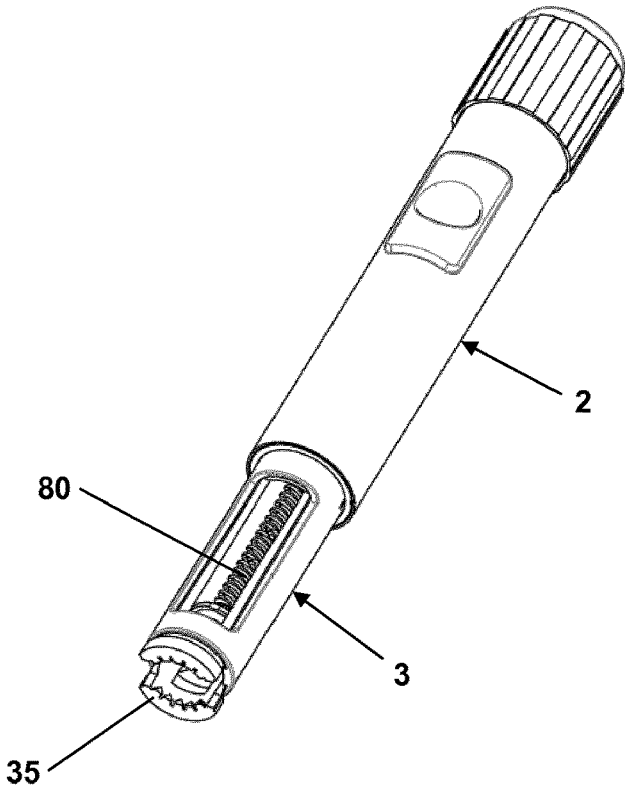

Referring to FIGS. 1A and 1B a pen-formed drug delivery device 1 will be described. More specifically, the pen device comprises a cap part (not shown) and a main part having a proximal body or drive assembly portion 2 with a housing 40 in which a drug expelling mechanism is arranged or integrated, and a distal cartridge holder portion in which a drug-filled transparent cartridge 90 with a distal needle-penetrable septum 92 is arranged and retained in place by a cartridge holder assembly 3 mounted to the proximal portion. The cartridge may for example contain an insulin, a GLP-1 or a growth hormone formulation. The device is designed to be loaded by the user with a new cartridge through a distal receiving opening in the cartridge holder assembly, the cartridge being provided with a piston driven by a piston rod 80 forming part of the expelling mechanism. A proximal-most rotatable dose setting member 70 serves to manually set a desired dose of drug shown in display window 50 and which can then be expelled when the release button 81 is actuated. In the shown drug delivery device the expelling mechanism comprises a spring which is strained during dose setting and then released to drive the piston rod when the release button is actuated. Alternatively the expelling mechanism may be fully manual in which case the dose setting member and the release button moves proximally during dose setting corresponding to the set dose size, and then moved distally by the user to expel the set dose. The cartridge is provided with distal coupling means in the form of a needle hub mount 95 having, in the shown example, an external thread adapted to engage an inner thread of a corresponding hub of a needle assembly. In alternative embodiments the thread may be combined with or replaced by other connection means, e.g. a bayonet coupling. The shown exemplary hub mount further comprises a circumferential flange with a number of distally facing pointed projections serving as a coupling means for the cartridge holder assembly as will be described in more detail below. A hub mount of the shown type is described in U.S. Pat. No. 5,693,027. Alternatively the needle hub mount may be formed as part of the cartridge holder, e.g. in the form of a "split" hub mount having two parts arranged on each of the gripping shoulders, see below.

As shown, the cartridge holder assembly 3 has the same general appearance as a traditional cartridge holder which is detachably coupled to the housing by e.g. a threaded coupling or a bayonet coupling and into which a new cartridge can be received as well as removed through a proximal opening, i.e. it comprises no additional user operated release or locking means. Instead, what appears merely to be the cartridge holder per se is in fact user operated coupling means in the form of an outer rotatable tube member 10 operated by the user to control movement of cartridge holding means in the form of an inner cartridge holder member 30 (see FIG. 2A) to thereby open and close gripping shoulders 35 configured to grip and hold a cartridge. More specifically, the gripping shoulder 35 is provided with a plurality of gripping teeth 38 spaced circumferentially to provide a plurality of gaps, each tooth having a triangular configuration with a proximally oriented pointed end, thereby creating a plurality of gaps having a distally oriented pointed configuration, this allowing the above-described distally facing pointed projections on the cartridge to be received between the teeth 38 to thereby serve as a gripping means when the cartridge holding means has been moved into engagement with the cartridge. In this way an easy-to-use front loaded drug delivery device is provided which appears as a traditional rear loaded device and which is also actuated by rotational movement to mount and remove a cartridge, the resemblance providing for ease of acceptance and adaptation among users accustomed to traditional types of rear loaded drug delivery devices.

When it is time to mount a new cartridge the outer tube member is rotated e.g. 90 degrees by which action the gripping shoulders 35 are moved distally and slightly outwards, this allowing the mounted cartridge to be removed. For ease of operation the cartridge may be moved distally a certain distance as the shoulders are moved, e.g. by engagement with arms forming the gripping shoulders and/or by additional spring means providing a biasing distally directed force. FIG. 1B shows the device with the cartridge removed and the gripping shoulders in their un-locked "open" position in which a cartridge can be removed and a new inserted. Depending on the design of the locking and actuation mechanism the gripping shoulders may be able to be left in the open position or they may be retracted automatically as the outer tube member is rotated backwards by return spring means. Whether or not a spring is provided the cartridge holder may be provided with locking means allowing the outer tube member to be securely parked in either the open or closed position, e.g. by a rotational snap lock. When a new cartridge is inserted the drive expelling means has to be in a state allowing the piston rod to be pushed proximally by the piston of the new cartridge. An exemplary embodiment of a coupling mechanism providing this functionality will be described below.

Figure 2A:
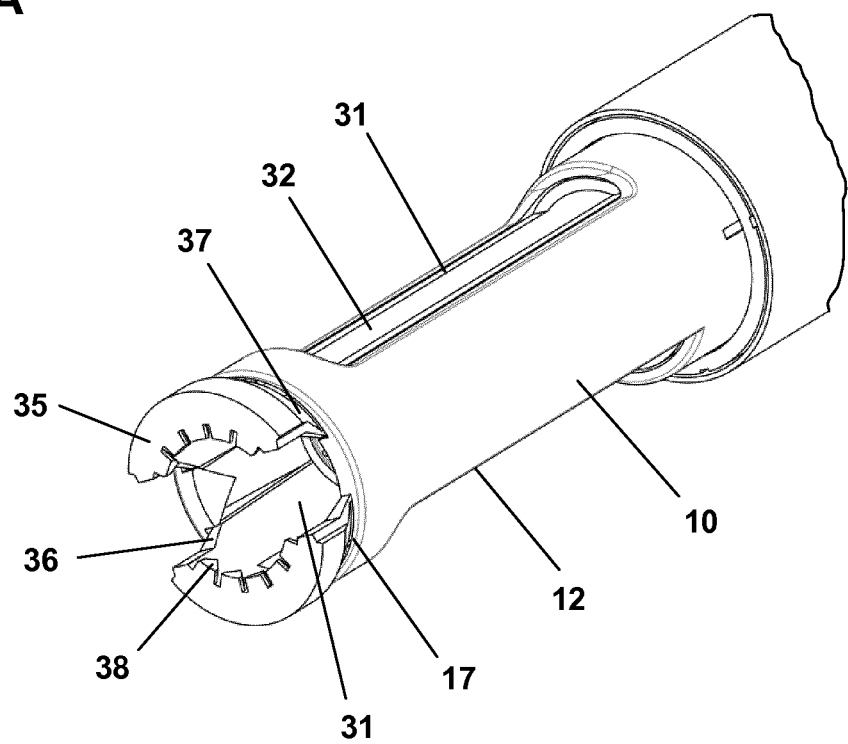
FIGS. 2A and 2B show detail views of the cartridge holder of FIG. 1A in an open respectively closed state.
Figure 2B:
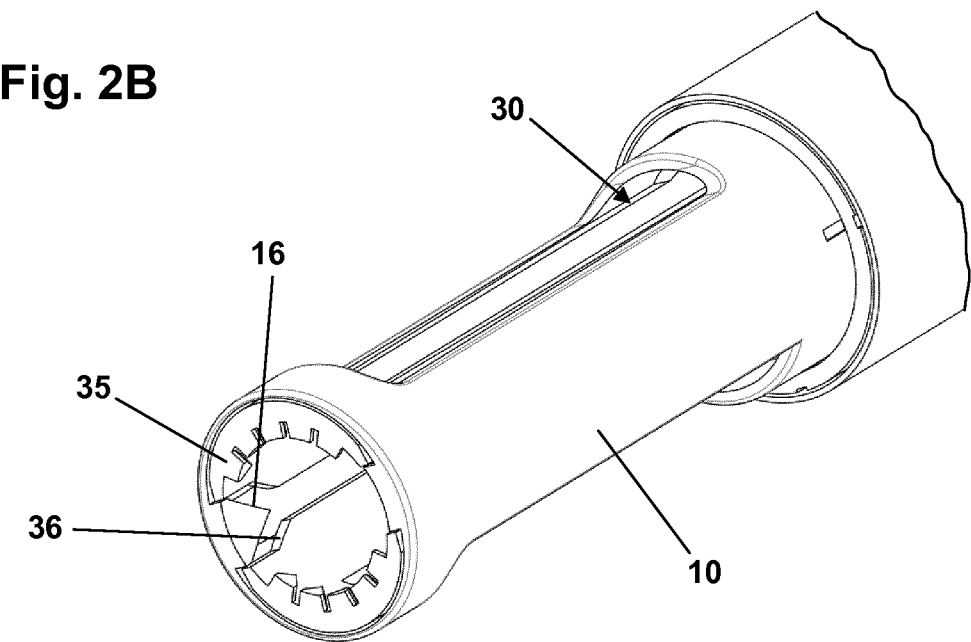

The mechanical arrangement providing the above-described user-interface, i.e. rotation of an outer tubular sleeve member moves gripping shoulders in and out, can be provided in numerous ways. As shown in FIGS. 2A and 2B the cartridge holder 30 comprises two opposed flexible arms 31 extending from a proximal ring portion arranged in axially guided sliding and thus non-rotational engagement with the outer tubular sleeve member, each arm being provided with a gripping shoulder 35. By this arrangement the gripping shoulders will rotate together with the outer tubular sleeve member and thus relative to the housing 40 as they are moved axially. In shown embodiment two opposed windows 32 are formed in the gripping member, one in each arm, each window being aligned with a corresponding window 12 formed in the outer tubular sleeve member, the two pairs of windows moving together in rotational alignment. Alternatively the gripping member and/or the outer tubular sleeve member may be manufactured fully or partly from a transparent material. Each gripping shoulder comprises an outer inclined and curved surface 37 adapted to engage a correspondingly curved distal actuation edge 17 of the outer tubular sleeve member 10, as well as a pair of inclined edge portions 36 adapted to engage a pair of corresponding inclined actuation surfaces 16 arranged on the inner surface of the actuation sleeve. By this arrangement the inclined actuation surfaces 36 will force the gripping shoulders outwardly to their open position as the actuation surfaces 36 are moved distally and into sliding contact with the sleeve actuation surfaces 16. Correspondingly, when the arms are moved proximally the outer curved surfaces 37 engage the actuation edges 17 and are thereby forced inwardly into their gripping position.

In alternative embodiments the gripping members may be arranged non-rotationally relative to the body portion 2, just as the actuation sleeve may be arranged to be moved axially only or by a combination of axial and rotational movement.

Figure 3:
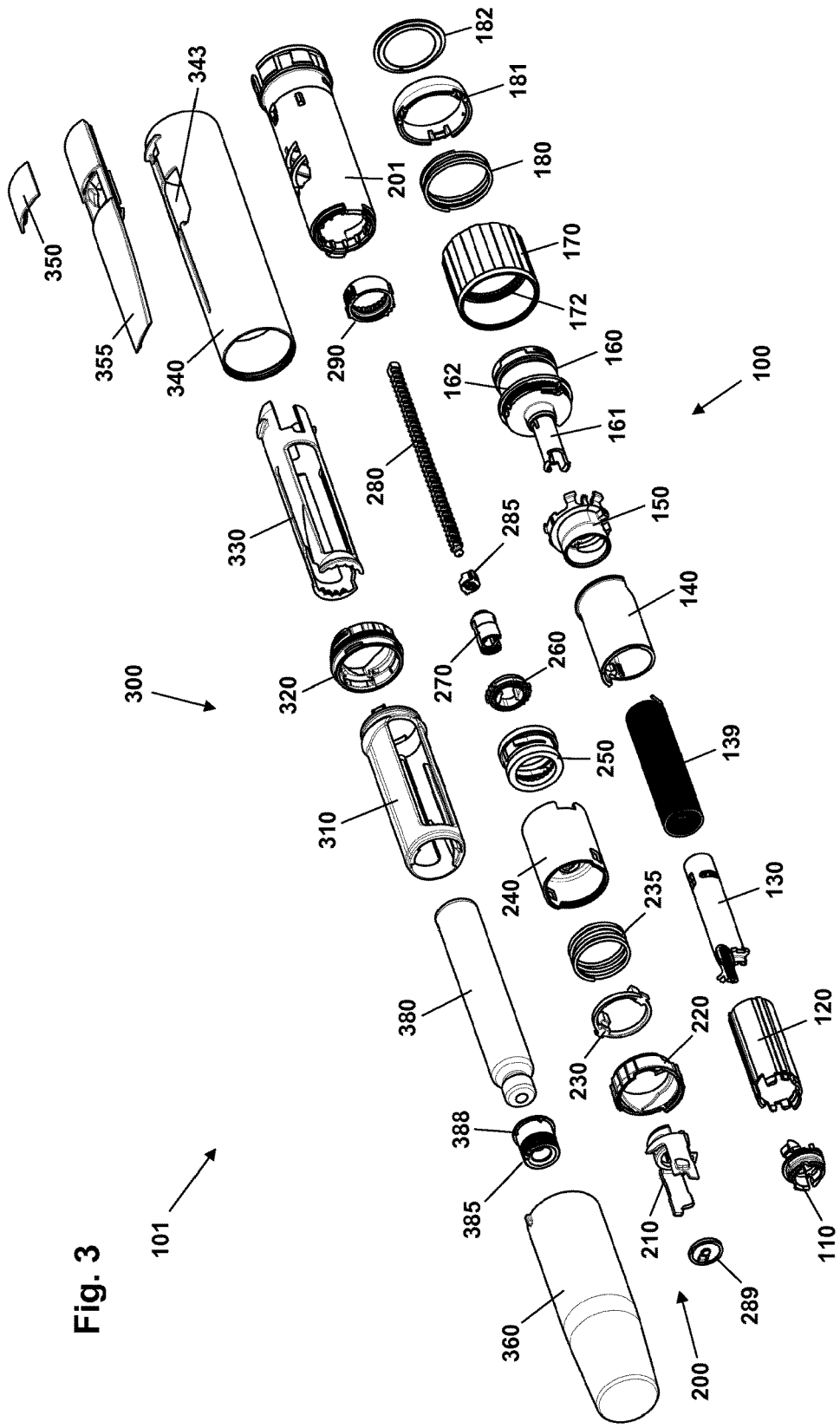
FIG. 3 shows in an exploded view components of a pen device of the type shown in FIG. 1A.
Figure 4:
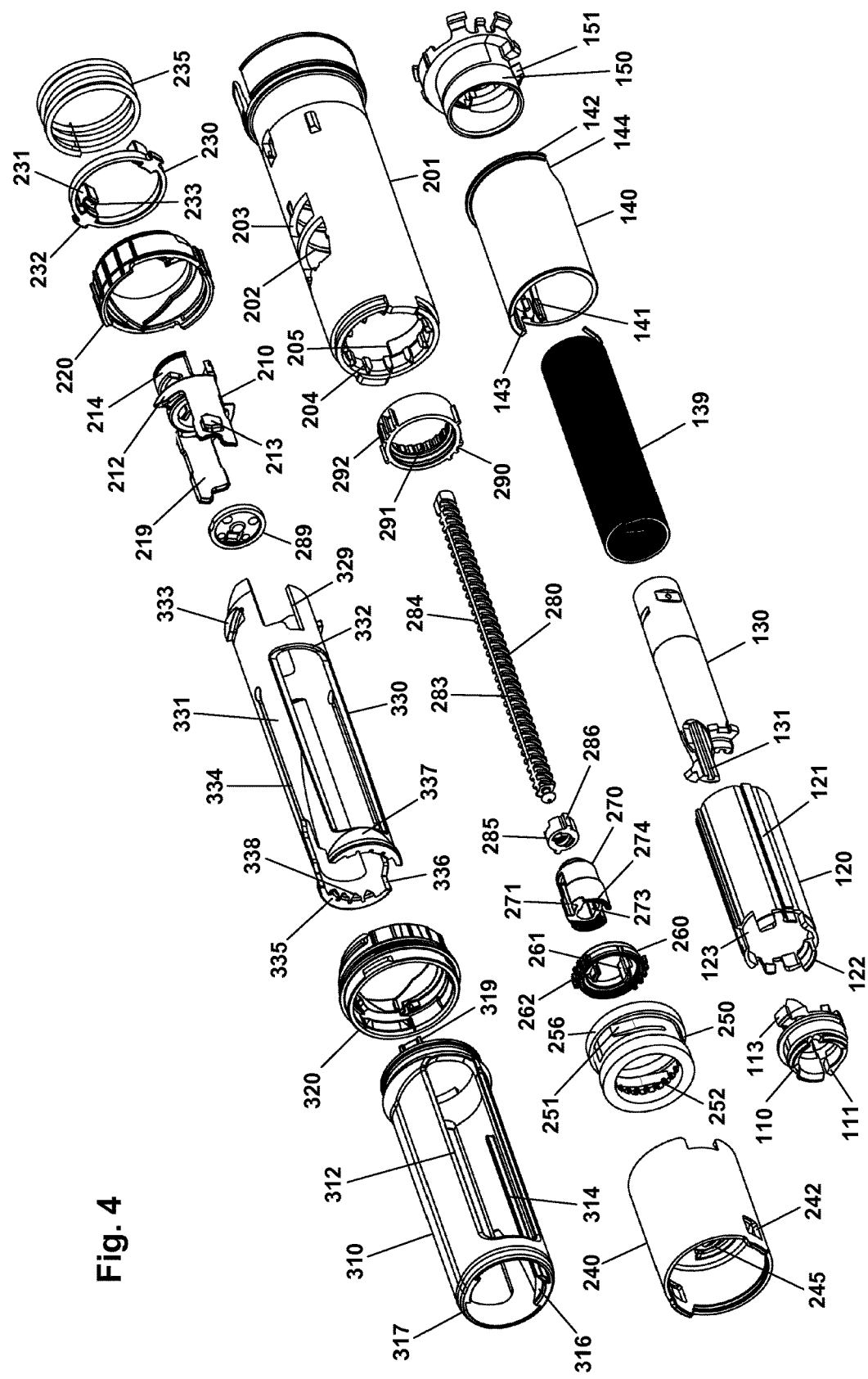
FIG. 4 shows in an exploded view a part of the components shown in FIG. 3.

FIG. 3 shows an exploded view of a pen-formed drug delivery device 101 of the type shown in FIGS. 2A and 2B. As aspects of the invention relate to the working principles of such a pen, an exemplary embodiment of a complete pen mechanism and its features will be described, most of which are merely illustrative examples of features and designs adapted to work with and support the aspects of the present invention. The pen will be described as comprising three assemblies, a dose setting assembly 100, a dose expelling and coupling assembly 200, and a cartridge holder and housing assembly 300. FIG. 4 corresponds to FIG. 3, however, to provide a better detail view some of the components are not shown and the remaining components have been rearranged.

More specifically, the dose setting assembly 100 comprises a ratchet member 110, a ratchet tube 120, a reset tube 130, a helical torque spring 139, a scale drum 140 with an outer helically arranged row of dose numerals (not shown), a spring base member 150, a button module 160, a user-operated dial member 170 for setting a dose of drug to be expelled, and a release button subassembly comprising a button ring 181, a button top window 182 and a button spring 180. The button module may be in the form a simple mechanical member adapted to be incorporated in the described mechanical design, or it may be in the form of an electronic module adapted to detect relative movement between different members in order to provide an electronic dose logging feature, however, the latter module version is incorporated in the same way as the simple version. The button window is adapted to be used when the button module is in the form of a logging module having a proximally facing display. Otherwise the button ring and top may be manufactured as a single button member. The proximal end of the reset tube member 130 is adapted to be connected rotationally and axially locked to the distal tube portion of the button module 160, however, this arrangement is mainly to allow the button part to be provided as a separate module, e.g. with or without electronic features.

Figure 14A:
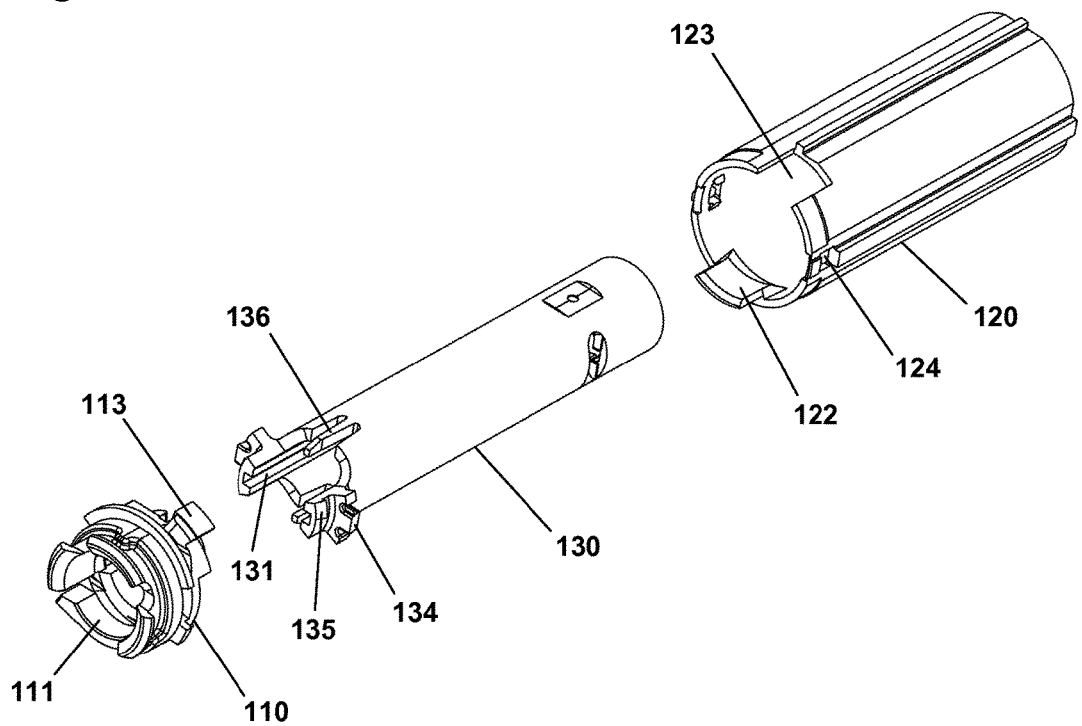
FIG. 14A shows in detail slightly modified versions of the components shown in FIG. 4.
Figure 14B:
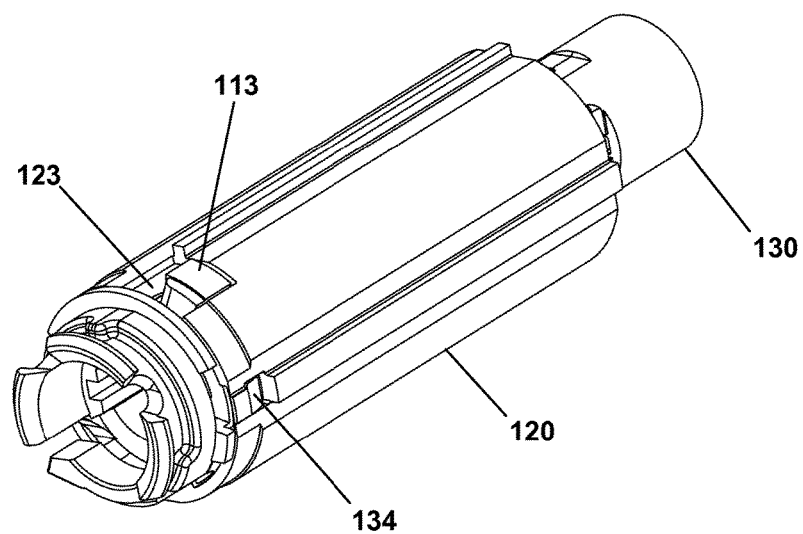
FIG. 14B shows the components of FIG. 14A in an assembled state.

Functionally, in an assembled state, the button module distal tube portion 161 is mounted axially and rotationally locked to the reset tube 130 which is mounted concentrically inside the ratchet tube 120, the two tubes being axially and rotationally locked at their distal ends, the latter arrangement being mainly for the purpose of moulding and subsequent assembly of the two components. However, the split design also allows the two members to be connected similar to a universal joint via projections 134 on the reset tube received in openings 124 on the ratchet tube (see FIG. 14A), this providing a mechanism with improved kinematic mobility being less over-constrained. Thus, during dose setting the dial member 170, the ratchet tube 120, the reset tube 130 and the button module 160 are rotationally locked forming a driver assembly.

The ratchet member 110 is mounted axially locked on the reset tube but is allowed to rotate a few degrees (see below) by means of axial snap connection means 135 on the reset tube, this "play" being controlled by the control projection 113 arranged in a ratchet tube cut-out 123. In this way a rotationally flexible connection is provided between the ratchet member and the reset tube, and thereby also between the ratchet member and the ratchet tube. More specifically, axially extending flexible arms 136 on the reset tube (see FIG. 14A) are received in the ratchet member, the flexible arms positioning the control projection 113 in the cut-out 123 such that there is no rotational play between the ratchet tube and the ratchet member during dose setting, however, during dose re-setting the ratchet member is allowed to move against the bias and corresponding to the rotational play provided between the projection 113 and the ratchet tube cut-out 123.

The reset tube comprises on its inner surface two opposed longitudinal grooves 131 adapted to engage radial projections 286 of the EOC member (see below), whereby the EOC can be rotated by the reset tube but is allowed to move axially. A clutch member 290 with outer spline elements is mounted axially locked on the ratchet member; this providing that the ratchet tube via the ratchet member can be moved axially in and out of rotational engagement with the housing via the clutch member. The dial member 170 is mounted axially locked but rotationally free on the inner housing proximal end. During dose setting the dial member is rotationally locked to the reset tube via toothed engagement with the button module (see below), rotation of the dial member thereby resulting in a corresponding rotation of the reset tube and thereby the ratchet tube and ratchet member. The release button 181 is axially locked to the reset tube via the button module but is free to rotate. The return spring 180 provides a proximally directed force on the button and the thereto mounted reset tube. The scale drum 140 is arranged in the circumferential space between the ratchet tube and the inner housing, the drum being rotationally locked to the ratchet tube via cooperating longitudinal splines 121, 141 and being in rotational threaded engagement with the inner surface of the inner housing via cooperating thread structures 142, 202, whereby the row of numerals passes window openings 203, 343 in the inner respectively outer housing (see below) when the drum is rotated relative to the housing by the ratchet tube. The proximal end of the scale drum comprises a stop surface 144 adapted to engage a corresponding stop surface 151 on the spring base member 150 to thereby provide a rotational stop for an initial (or end) rotational position, and the distal end of the scale drum comprises a further stop surface 143 adapted to engage a corresponding stop surface 205 on the proximal housing inner surface when the maximum dose has been reached during dose setting, e.g. 100 units of insulin (IU). The torque spring 139 is arranged in the circumferential space between the ratchet tube and the reset tube and is at its proximal end secured to the spring base member 150 and thus the housing and at its distal end to the ratchet member 110, whereby the spring is strained when the ratchet member is rotated relative to the housing by rotation of the dial member. A ratchet mechanism with a flexible ratchet arm 111 is provided between the ratchet member and the clutch member, the latter being provided with an inner circumferential teeth structure 291 (or toothing), each tooth providing a ratchet stop such that the ratchet tube is held in the position to which it is rotated by a user via the reset tube when a dose is set. In order to allow a set dose to be reduced a ratchet release mechanism in the form of a release member 122 is provided on the ratchet tube and acting on the ratchet member to move it inwards and thereby out of engagement with the teeth structure, this allowing a set dose to be reduced by one or more ratchet increments by turning the dial member in the opposite second direction, the release mechanism being actuated when the ratchet tube is rotated the above-described few degrees of play relative to the ratchet member. Alternatively the release mechanism could be arranged on the reset tube.

The dose expelling and coupling assembly 200 comprises a fork member (or "slider") 210, a distal housing 220, a ring member 230, a compression spring 235, a nut housing 240 comprising a central portion with a threaded nut bore 245, a drive assembly comprising an outer drive member 250, a coupling member 260 and an inner drive member 270, a threaded piston rod 280 having an external thread 284 and two opposed longitudinal planar surfaces 283, an end-of-content (EOC) member 285, a piston rod washer 289, a clutch member 290 and a proximal housing 201.

Functionally, in an assembled state, the inner drive member 270 comprising a central bore with two opposed planar surfaces is mounted axially locked but rotationally free on the central portion of the nut housing 240 by means of a circumferential flange 244 (see FIG. 8) surrounding the proximal opening of the nut bore and a pair of opposed gripping flanges 274 arranged on the distal end of the inner drive member. The central nut portion is carried in the nut housing by arm structures 246 (see FIG. 8) providing openings through which the proximal-most part 214 of the fork element is arranged. The piston rod is arranged through the two aligned bores with the threaded bore 245 receiving the piston rod thread 284 and with the two opposed planar surfaces 273 of the inner drive member in engagement with the opposed planar surfaces 283 on the piston rod, whereby rotation of the inner drive member results in rotation and thereby distal axial movement of the piston rod due to the threaded engagement between the piston rod and the nut bore. On the piston rod the end-of-content (EOC) member 285 is threadedly mounted and on the distal end the washer 289 is axially mounted but rotationally free. The washer can be considered the part of the piston rod which is adapted to directly engage a cartridge piston. The EOC member comprises a pair of opposed radial projections 286 for engagement with the reset tube (see above).

The ring-formed outer drive member 250, which is mounted axially locked but rotationally free in the nut housing, is in permanent rotational engagement with the ring-formed clutch member 290 by means of cooperating coupling structures, such that the engagement allows axial movement of the clutch member relative to the outer drive member. The outer drive member further comprises a pair of opposed circumferentially extending flexible ratchet arms 251 adapted to uni-directionally engage corresponding ratchet teeth 241 (see FIG. 7A) arranged on the nut housing inner surface. In the embodiment of FIG. 4 the outer drive member is provided with a proximal supporting ring structure 256. The clutch member is provided with outer spline elements 292 adapted to engage corresponding spline elements 204 on the proximal housing inner surface, this allowing the clutch member to be moved between a rotationally locked proximal position, in which the splines are in engagement with the inner housing, and a rotationally free distal position in which the splines are out of engagement with the inner housing.

Between the outer and inner drive members the ring-formed coupling member 260 is arranged, this providing that the drive assembly can be actuated between a resetting state (see below) in which the inner drive member and thereby the piston rod can be rotated relative to the outer drive member and thereby the nut housing, and an operational state in which the inner and outer drive members are rotationally locked to each other. The coupling member is mounted axially locked but rotationally free on the proximal end portion 214 of the fork member 210, as well as rotationally locked but axially free on the inner drive member via cooperating spline structures 261, 271. The coupling member comprises circumferentially arranged outer coupling teeth 262 adapted to be moved axially in and out of engagement with corresponding coupling teeth 252 arranged circumferentially on the inner surface of the outer drive member. By this arrangement the coupling member can be actuated via axial movement of the fork member between a proximal position in which the coupling member and outer drive member are rotationally disengaged, this corresponding to the resetting state, and a distal position in which the coupling member and outer drive member are rotationally engaged, this corresponding to the operational state. As will be described below, the fork member is actuated during user-operated cartridge change.

By providing a drive assembly with an "internal" coupling member as the axially actuated coupling component, it is possible to mount both the outer and inner drive members axially fixed as described above, this allowing e.g. the inner drive member in cooperation with the EOC member to serve as part of a safety system, this as described in WO 2007/017053.

The ring member 230 is mounted rotationally locked but axially free to the nut housing 240 and is biased distally by the compression spring 235, the ring thereby providing a distally directed force on an inserted cartridge. The functionality of the ring member as well as the distal housing 220 will be described together with components of the cartridge holder and housing assembly.

The cartridge holder and housing assembly 300 comprises a cap member 360, a user operated generally tubular actuation sleeve 310, a ring-formed sleeve mount 320, a cartridge holder 330, and an outer housing assembly comprising a tubular housing member 340, a magnifier lens 350, and a clip member 355 also serving as a lens mount. The cartridge holder is adapted to receive and hold a generally cylindrical drug-filled cartridge 380 provided with distal coupling means in the form of a needle hub mount 385 having, in the shown example, an external thread adapted to engage an inner thread of a corresponding hub of a needle assembly. In alternative embodiments the thread may be combined with or replaced by other connection means, e.g. a bayonet coupling. The hub mount further comprises a circumferential flange with a number of distally facing pointed projections 388 serving as a coupling means for the cartridge holder assembly as will be described in more detail below. A hub mount of the shown type is described in U.S. Pat. No. 5,693,027.

Functionally, in an assembled state, the cartridge holder 330 is mounted rotationally locked but axially free inside the actuation sleeve 310 which is mounted axially locked but rotationally moveable to the sleeve mount 320 which again is mounted axially and rotationally locked to the distal housing. The fork member 210 is mounted rotationally locked but axially free to the cartridge holder by means of the two fork legs 219 being received in opposed slots 339 formed in the cartridge holder. As will be described in detail below the combined sleeve mount and distal housing provide an inner circumferential control track in which pairs of opposed lateral control protrusions 333, 213 of respectively the cartridge holder and the fork member are received, the track providing controlled axial movement of respectively the cartridge holder and the fork member when the two components are rotated relative to the track by means of the user rotating the actuation sleeve. The sleeve mount is further provided with two pairs of stop surfaces 329 (see FIG. 5A) adapted to engage corresponding lateral stop surfaces provided on a pair of control extensions 319 arranged on the proximal end of the actuation sleeve, the stop surfaces providing rotational stops for the actuation sleeve.

The cartridge holder comprises a pair of opposed flexible arms 331 extending from a proximal ring portion, each arm being provided with a distal gripping portion, or "jaw", 335 having a plurality of proximal facing gripping teeth 338 spaced circumferentially to engage the above-described distally facing pointed projections 388 on the cartridge. A pair of longitudinally oriented opposed slots is formed between the arms, the slots each receiving a longitudinally oriented spline 314 formed on the inner surface of the actuation sleeve, this providing axially guided non-rotational engagement with the sleeve. Two opposed windows 332 are formed in the cartridge holder, one in each arm, each window being aligned with a corresponding window 312 formed in the outer tubular sleeve, the two pairs of windows moving together in rotational alignment. Corresponding to the embodiment of FIG. 2B each gripping portion 335 comprises an outer proximally-facing inclined and curved surface 337 adapted to engage a correspondingly curved distal circumferential edge 317 of the sleeve member 310, as well as a pair of inclined distally-facing edge portions 336 adapted to engage a pair of corresponding inclined proximally facing actuation surfaces 316 arranged on the inner surface of the actuation sleeve. By this arrangement the inclined actuation surfaces 336 will force the gripping shoulders outwardly to their open position as the actuation surfaces 336 are moved distally and into sliding contact with the sleeve actuation surfaces 316. Correspondingly, when the arms are moved proximally the outer curved surfaces 337 engage the actuation edges 317 and are thereby forced inwardly into their gripping position. As indicated above, axial movement of the cartridge holder is controlled by the cartridge holder control protrusions 333 being rotated in the control track by means of rotating the actuation sleeve.

As described above, the fork member is rotationally coupled to the cartridge holder via fork legs 219 and correspondingly rotates together therewith when the actuation sleeve is rotated, axial movement being controlled by the fork control protrusions 213 being received in the control track. To ensure that the piston rod is free to be pushed proximally during cartridge insertion, actuation of the cartridge holder between its receiving and gripping state and actuation of the drive coupling via the fork member take place in sequence. More specifically, in the shown embodiment full actuation of the cartridge holder takes place during a 60 degrees rotation of the actuation sleeve during which the fork member is not moved axially. When the cartridge thus has been properly locked in place and the piston rod correspondingly has been pushed to a corresponding proximal position, a subsequent 30 degrees further rotation of the actuation sleeve results in the drive coupling being actuated between the resetting state and the operational state by means of the fork member being moved distally during which the cartridge holder is not moved axially. In this way it is ensured to a high degree that the piston rod washer is positioned just in contact with the cartridge piston without build-up of tension in the system or creation of an air gap between the piston rod washer and the cartridge piston.

The ring member 230 comprises a ring portion, a pair of opposed radial guide protrusions 232 adapted to engage corresponding openings 242 in the nut housing, and a pair of opposed proximal protrusions 231. The latter each has a distal surface 233 adapted to engage the proximal edge of an inserted cartridge, as well as a proximal stop surface adapted to engage a corresponding distal stop surface on the fork member. For that purpose the fork member comprises a pair of circumferential arms 212 each providing a distal stop surface. As appears, the ring portion which encircles the cartridge holder merely serves as a carrier for the different protrusions. To prevent a user inserting a cartridge too deep into the cartridge holder, the ring member is actuated between a receiving and an operational state. More specifically, when the cartridge holder is in the initial receiving state with the gripping portions 335 fully apart, the user will insert the cartridge against the biasing force provided by the ring member. However, to prevent the cartridge from being pushed too deeply into the cartridge holder, the fork member provides via the above-described stop surfaces a proximal stop for the ring member, the stop position corresponding to a position somewhat distally of the fully inserted position. As the user then starts to rotate the actuation sleeve and the gripping portions are moved proximally the fork member stop surfaces 212 are rotated out of engagement with the ring member which is then allowed to be moved to its operational position as the cartridge is moved proximally by means of the gripping portions. In a front-loaded drug delivery device such an arrangement helps ensure that a cartridge is not inserted too deeply during initial loading of a cartridge, i.e. it can be prevented that the user pushes the piston rod too far proximally when the cartridge is inserted and thereby creates an air gap between the piston rod and the cartridge piston in the operational state in which the cartridge is mounted in the cartridge holder and the piston rod is locked in its operational state. As appears, depending on the actual design of the control track, the locking arms may start move proximally before the stop surfaces are rotated out of engagement with the ring member, however, to avoid tension in the system, the ring member should be free to move proximally when the gripping arms engage the cartridge and start pulling it proximally towards the biasing force from the ring member.

To prevent the user from releasing the expelling mechanism before the actuation sleeve has been fully rotated to its operational position, the fork member also serves to prevent a set and strained expelling mechanism from being released. More specifically, until the drive coupling is in the operational state the proximal-most surface of coupling member mounted on the fork element serves as a stop for the ratchet assembly thereby preventing the clutch member from being moved distally out of engagement with the housing and thus released. A further mechanism preventing a user from releasing the expelling mechanism before a cartridge has been mounted will be described below with reference to FIGS. 9A and 9B.

The outer housing 340 mainly serves to protect the interior components and to provide stiffness and an attractive outer appearance. Especially, the outer housing covers all the joints of the different inner housing parts.

Having described the individual components as well as the structural and functional relationship with reference to the exploded views of FIGS. 3 and 4, the functionality of certain subsystems will be described in greater detail with reference to FIGS. 5-9 illustrating the structural and functional interaction between individual components.

Figure 5A:
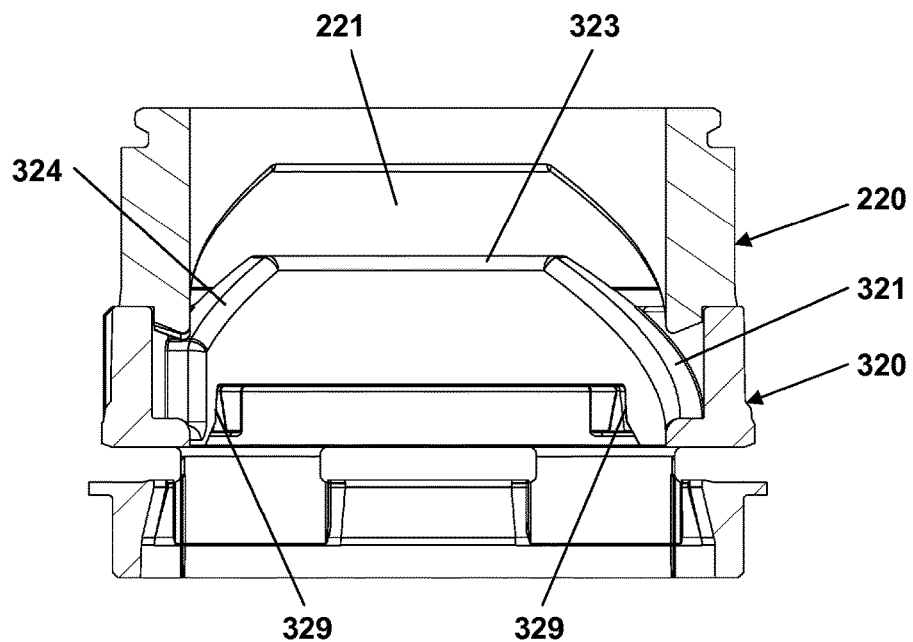
FIG. 5A shows in a sectional view a control track assembly.
Figure 5B:
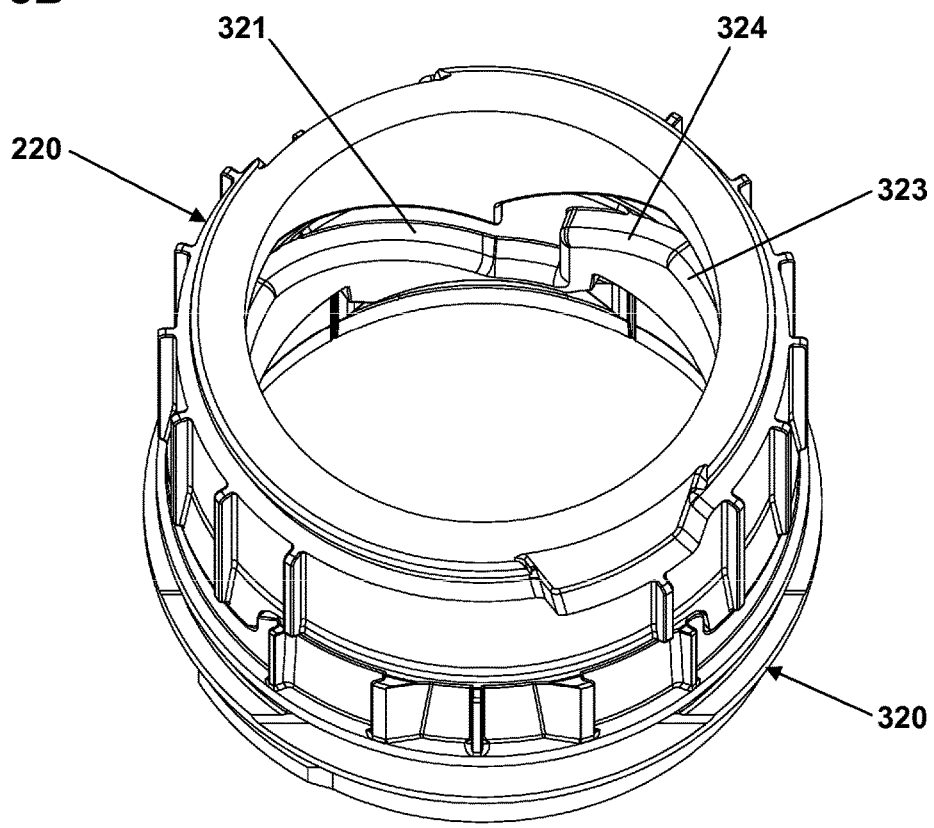
FIG. 5B shows in a perspective view the control track assembly.

More specifically, FIG. 5A shows in a sectional view a full 180 degrees half portion of the control track 221 responsible for axial movement of one cartridge holder control protrusion and one fork member control protrusion, the opposed other half of the control track being into engagement with the other two control protrusions. The control track is formed by the sleeve mount 320 and the distal housing 220 in combination. FIG. 5B shows in a perspective view a portion of the control track. The shown track portions comprise (reference numerals refer to the sleeve part of the track) a cartridge holder slope portion 321 on the sleeve mount, an intermediate axially equidistant portion 323, and a fork member slope portion 324.

Figure 6A:
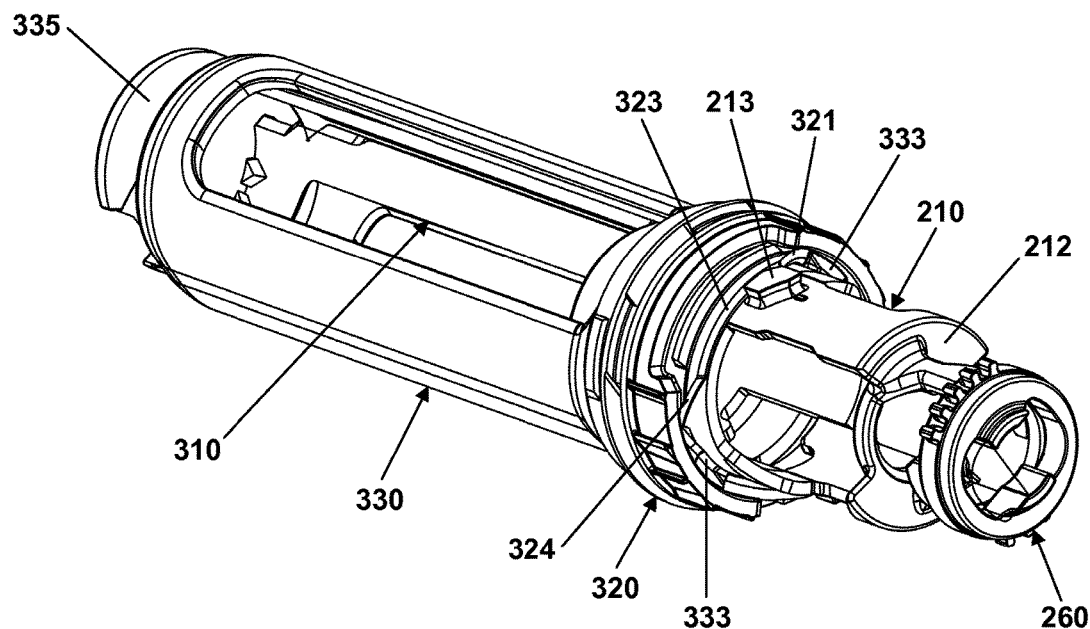
FIGS. 6A-6C show in perspective views a cartridge holder assembly in different operational states.
Figure 6B:
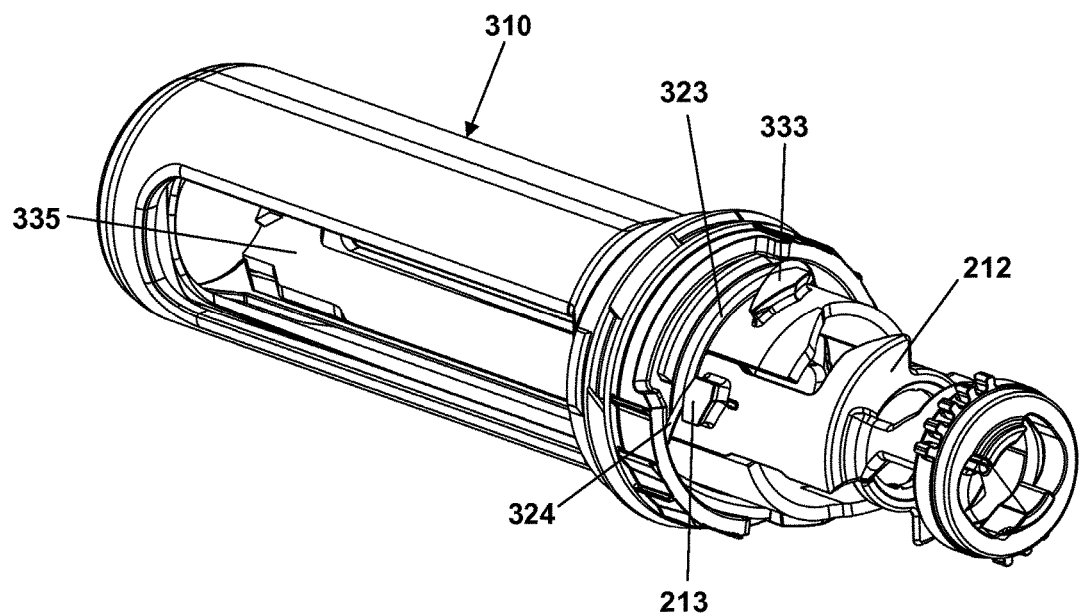
Figure 6C:
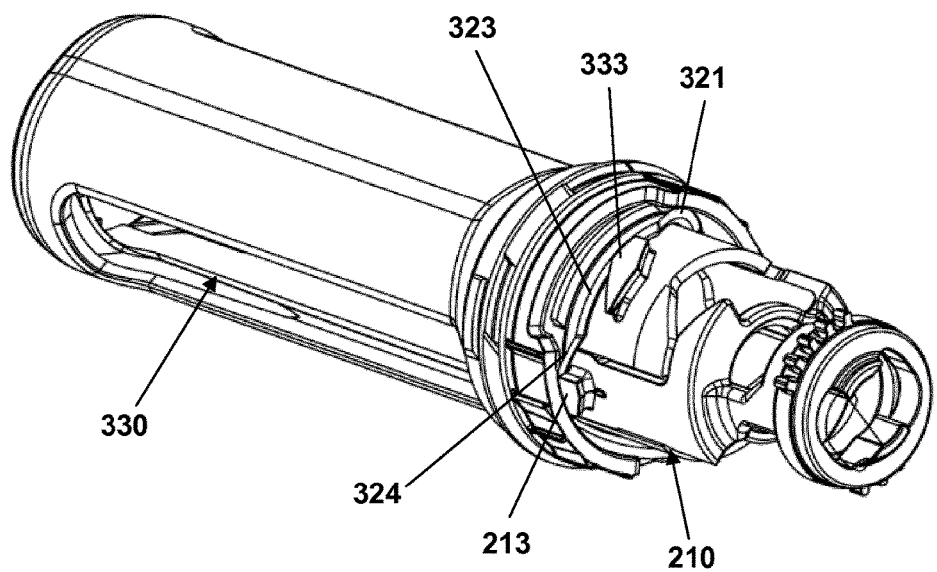

FIGS. 6A-6C illustrate in different operational states a cartridge holder assembly comprising the above-described cartridge holder 330, fork member 210, actuation sleeve 310, sleeve mount 320, and coupling member 260. As described above, the actuation sleeve is rotatable mounted in the sleeve mount which is mounted to the distal housing 220 to thereby form the control track, the cartridge holder is axially displaceable mounted in the actuation sleeve with the control protrusions 333 arranged in the control track, the fork member is axially displaceable mounted in the cartridge holder with the control protrusions 213 arranged in the control track, and the coupling member 260 is rotatable mounted on the fork member distal end. When the actuation sleeve is rotated the cartridge holder and therewith the fork member are rotated as well as moved axially via engagement with the control track. As the coupling member is rotationally locked to the inner drive member 270 it does not rotate relative to the piston rod, however, as the piston rod is pushed proximally during cartridge loading the piston rod and thereby the coupling member will rotate relative to the housing.

During cartridge loading for the shown embodiment the following operations take place. With the cartridge holder in its receiving state with the gripping portions 335 fully apart and in their distal-most position a used cartridge can be removed and a new cartridge can be inserted, this at the same time providing that the piston rod, which initially is positioned corresponding to the position of the piston in the used cartridge, is pushed proximally. As shown in FIG. 6A the cartridge holder control protrusions 333 are positioned in the distal end of the cartridge holder slope portions, and the fork member control protrusions 213 are positioned in the intermediate track portions just next to the cartridge holder slope portions.

Actuation of the cartridge holder then takes place during a 60 degrees rotation of the actuation sleeve during which the gripping portions are moved inwards and retracted to their proximal-most holding position. In this intermediate state the cartridge has been properly locked in place and the piston rod correspondingly has been pushed to a corresponding proximal position. The fork member is not moved axially during this operation but merely rotates. More specifically as shown in FIG. 6B, during the initial 60 degrees rotation of the actuation sleeve 310 the cartridge holder control protrusions 333 are moved proximally in the cartridge holder slope portions 321 and into the intermediate track portions 323 just next to the cartridge holder slope portions, and the fork member control protrusions 213 are moved in the intermediate track portions from just next to the cartridge holder slope portions to just next to the fork member slope portions 324.

Actuation of the drive coupling then takes place during a further 30 degrees rotation of the actuation sleeve during which the fork member is moved to its distal-most position with the coupling member in engagement with the outer drive member 250. The cartridge holder 330 is not moved axially during this operation but merely rotates. More specifically as shown in FIG. 6C, during the further 30 degrees rotation of the actuation sleeve the fork member 210 control protrusions 213 are moved distally in the fork member slope portions 324, and the cartridge holder control protrusions 333 are moved in the intermediate track portions 324 from just next to the cartridge holder slope portions 321 to the middle portion of the intermediate track portions 323. In this way it is ensured to a high degree that the piston rod washer is positioned just in contact with the cartridge piston without build-up of tension in the system.

When a loaded cartridge is to be replaced the above-described operations are performed in the reverse order by rotating the actuation sleeve a full 90 degrees in the opposite direction, whereby first the drive coupling disengages and then the cartridge holder is moved from its proximal holding position to its distal receiving position.

Although FIGS. 6A-6C for illustrative purposes do not show the ring member 230, it can be seen how the circumferential arms 212 of the fork member 210 is rotated during the initial cartridge holder actuation, thereby rotationally retracting the stop surfaces for the ring member, this allowing the biased ring member to be moved proximally by the cartridge.

With reference to FIGS. 6A-6C the combined actuation mechanism for the cartridge holder and the drive coupling was described. Next with reference to FIGS. 7A-7C the same operational states will be described focusing on the actual coupling elements per se.

Figure 7A:
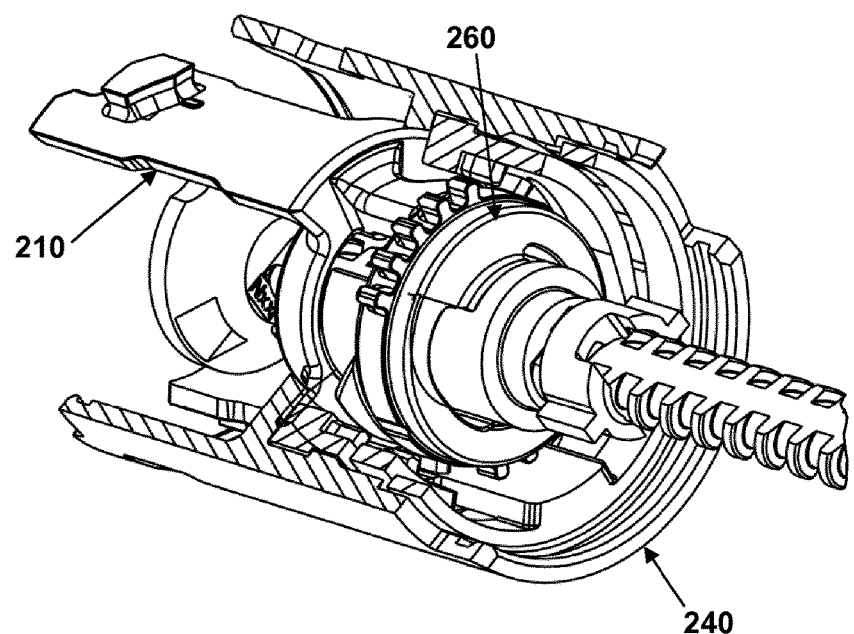
FIGS. 7A-7C show in perspective views a coupling assembly in operational states corresponding to FIGS. 6A-6C, FIG. 8 corresponds to FIG. 7A with some structures removed.
Figure 7B:
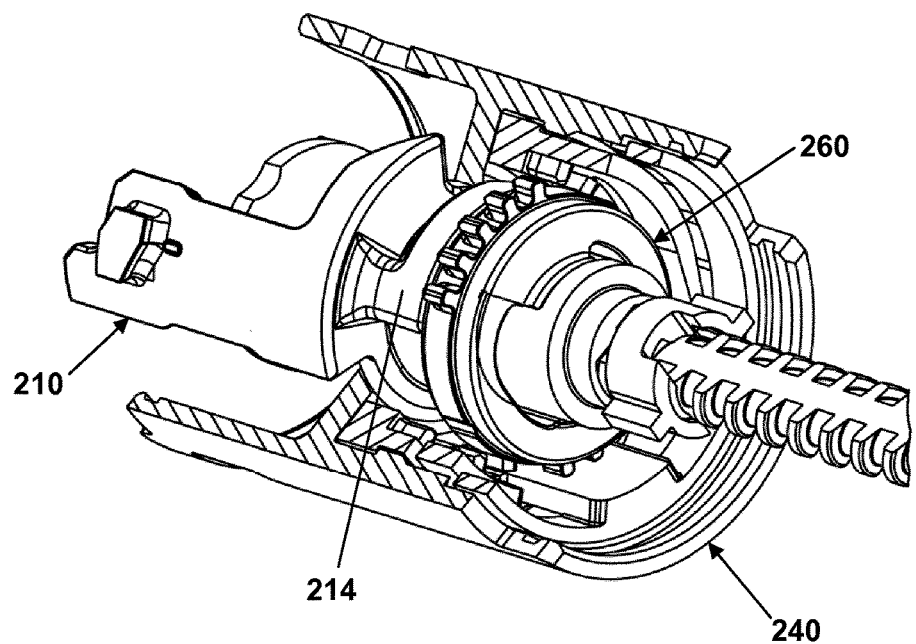
Figure 7C:
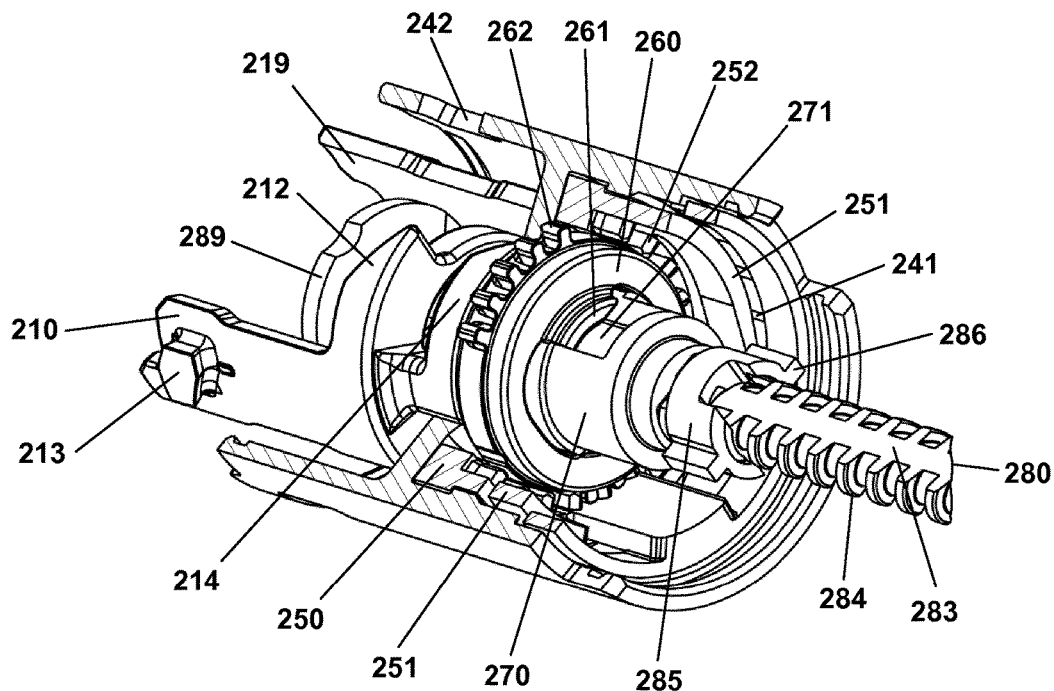

More specifically, FIG. 7C (providing the best view of the components) illustrates a coupling assembly comprising the above-described fork member 210, nut housing 240, the drive assembly comprising the outer drive member 250, the coupling member 260 and the inner drive member 270, the threaded piston rod 280, the EOC member 285 and the piston rod washer 289.

As described above, the inner drive member 270 is mounted axially locked but rotationally free on the central portion of the nut housing 240 by means of the circumferential flange 244 (see FIG. 8) surrounding the proximal opening of the nut bore and the pair of opposed gripping flanges 274 arranged on the distal end of the inner drive member. The piston rod is arranged through the two aligned bores with the threaded bore receiving the piston rod thread and with the two opposed planar surfaces 273 (see FIG. 4) of the inner drive member in engagement with the opposed planar surfaces 283 on the piston rod. On the piston rod the EOC member 285 and the washer 289 are mounted. The outer drive member 250 is mounted axially locked but rotationally free in the nut housing with the flexible ratchet arms 251 uni-directionally engaging the ratchet teeth 241 arranged on the nut housing inner surface.

The coupling member 260 is mounted axially locked but rotationally free on the proximal end portion 214 of the fork member 210, as well as rotationally locked but axially free on the inner drive member 270 via the cooperating spline structures 261, 271. The coupling member comprises circumferentially arranged outer coupling teeth 262 adapted to be moved axially in and out of engagement with the corresponding coupling teeth 252 arranged circumferentially on the inner surface of the outer drive member. By this arrangement the coupling member can be actuated via axial movement of the fork member (as described above with reference to FIGS. 6A-6C) from a proximal position in which the coupling member and outer drive member are rotationally disengaged (see FIG. 7A), this corresponding to the resetting state, via the intermediate state in which the fork member has been rotated but not moved axially (see FIG. 7B), to a distal position in which the coupling member and outer drive member are rotationally engaged, this corresponding to the operational state as shown in FIG. 7C.

Figure 8:
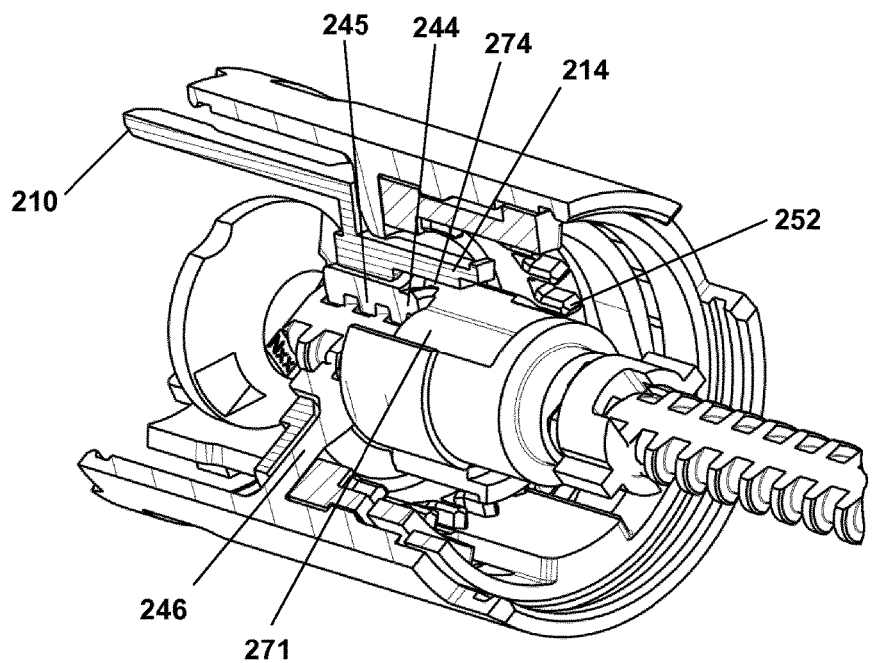

FIG. 8 corresponds to FIG. 7A, however, to better illustrate the mounting of the inner drive member 260 on the central nut portion via the above-described bearing structures 244, 274 the coupling member has been removed and the fork member 210 partially cut away.

Figure 9A:
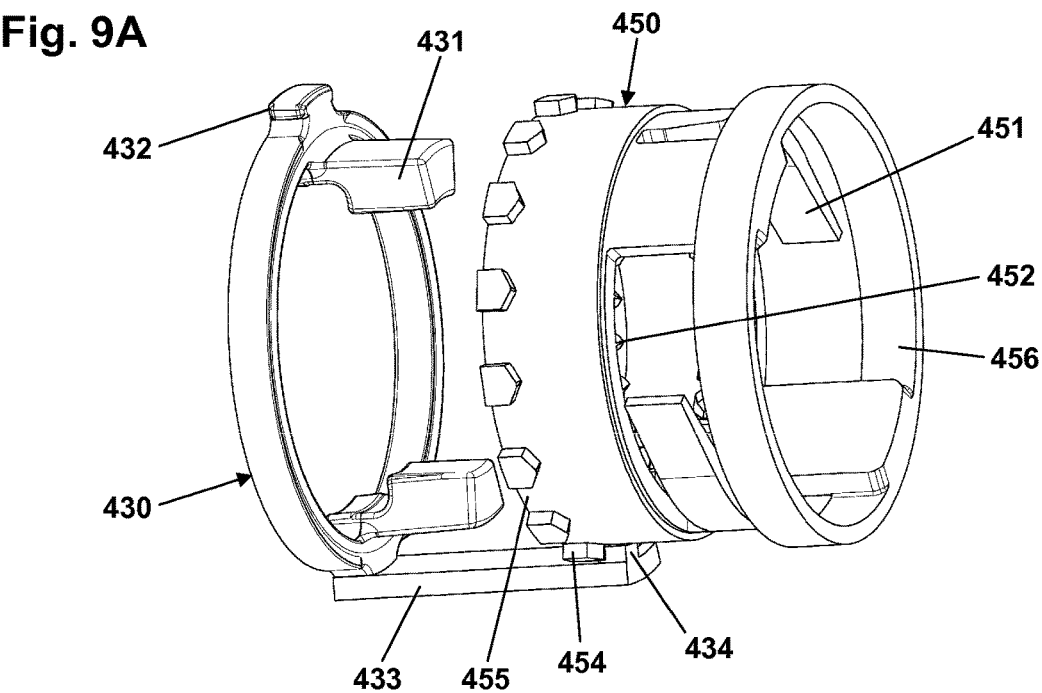
FIGS. 9A and 9B show in perspective views an alternative coupling assembly in different operational states.
Figure 9B:
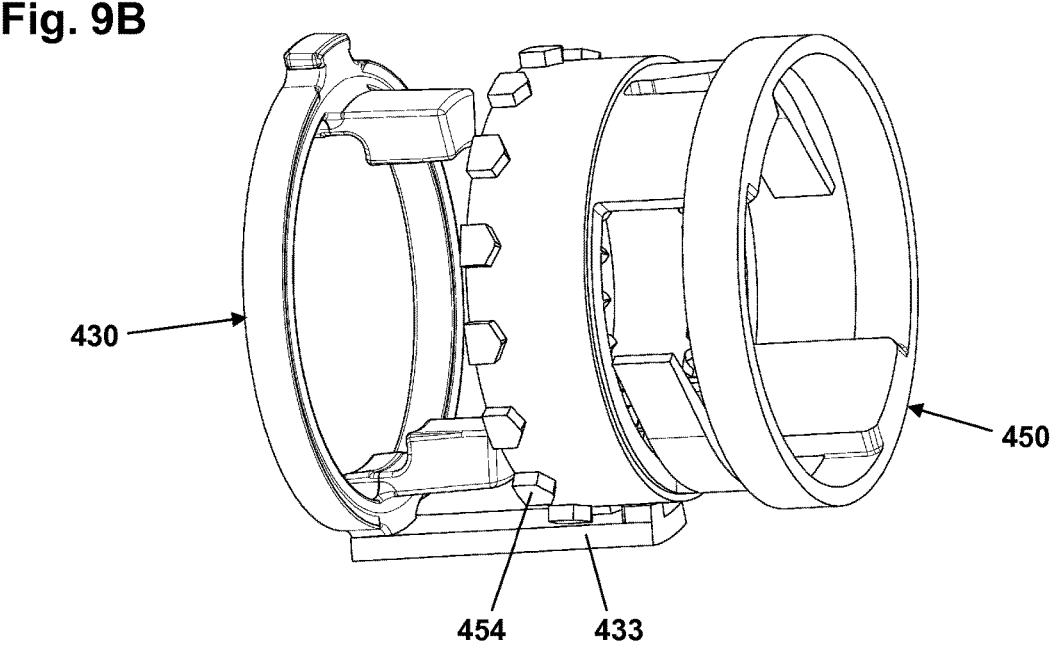

With reference to FIGS. 9A and 9B an alternative configuration of the ring member 230 and the outer drive member 250 of FIG. 4 will be described, the members having been modified to provide a lock against release of a set and strained expelling mechanism unless a cartridge has been loaded in the cartridge holder, irrespective of the state of the cartridge holding assembly.

More specifically, the ring member 430 comprises as the above-described ring member 230 a pair of opposed radial guide protrusions 432 adapted to engage openings in the nut housing, and a pair of opposed proximal protrusions 431. A control arm 433 extends proximally from one of the lateral guide protrusion as is provided with an inner control protrusion 434. The control arm is guided in a corresponding longitudinal slot in a modified nut housing (not shown). The outer drive member 450 comprises as the above-described outer drive member 250 a pair of opposed ratchet arms 451, a plurality of coupling teeth 452 as well as a proximal supporting ring portion 456, however, in addition a plurality of teeth structures 454 are arranged circumferentially on the outer distal surface, the equidistantly arranged teeth providing a plurality of gaps 455 each configured to accommodate the control protrusion 434. When no cartridge is inserted in the cartridge holder the ring member and thereby also the control protrusion 434 is biased to its distal-most position by spring 235, whereby as shown in FIG. 9A the control protrusion is seated between two teeth structures 454 thereby preventing rotation of the outer drive member. When a cartridge has been loaded in the cartridge holder the ring member and thereby also the control protrusion 434 has been moved proximally and out of engagement with the outer drive member. When the cartridge is removed the spring 235 will return the ring member to its initial position and thereby move the control protrusion into blocking engagement with the outer drive member as shown in FIG. 9B. To facilitate seating of the control protrusion between the teeth both structures are provided with pointed surfaces on their facing ends.

Figure 10A:
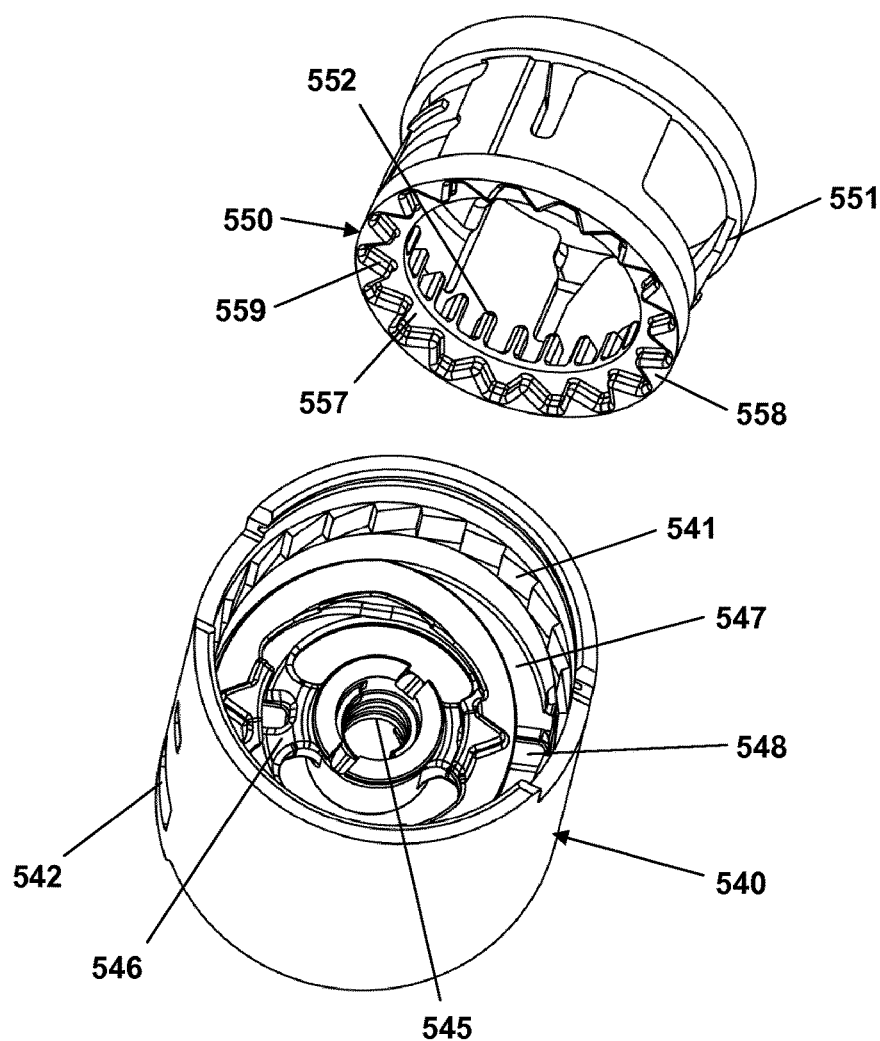
FIGS. 10A and 10B show components for a rotational brake for an expelling mechanism.
Figure 10B:
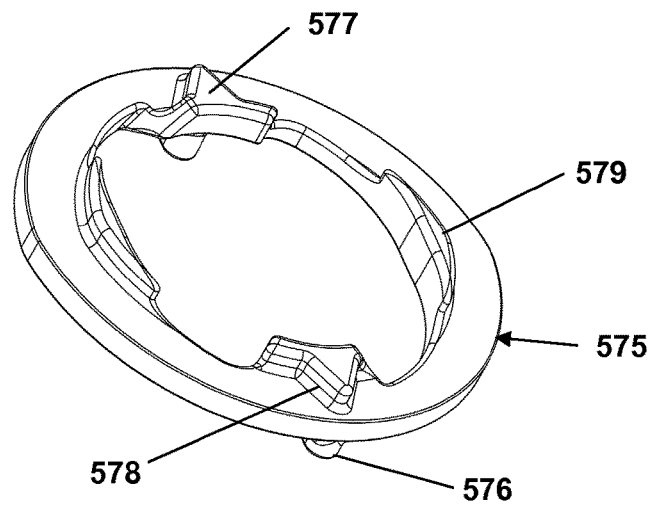

With reference to FIGS. 10A and 10B an alternative configuration of the nut housing 240 and the outer drive member 250 of FIG. 4 will be described, the modifications in combination with a further brake member 575 arranged between the two members providing a rotational brake for the expelling mechanism.

More specifically, the modified nut housing 540 comprises as the FIG. 4 embodiment a central nut portion with a threaded bore 545 being carried in the nut housing by supporting arm structures 546, circumferentially arranged ratchet teeth 541 on the nut housing inner surface and distal guide openings 542. The main additional features of the modified nut housing is a circumferential flange with a proximal sliding surface 547 for the brake member 575 as well as a pair of opposed radial guide grooves 548 formed in the flange proximal surface and arranged generally corresponding to the location of the support arms 546. The modified outer drive member 550 comprises as the FIG. 4 embodiment a pair of ratchet arms 551 and a plurality of circumferentially arranged coupling teeth 552, whereas the support ring portion 256 has been removed. The main additional feature of the modified outer drive member is an uneven number of circumferentially arranged brake teeth structures 558 arranged on the distally facing circumferential surface 557. Each brake tooth has a general triangular configuration with an inner axially facing point, two neighbouring inclined surfaces (one of which serves as a brake surface 559), an outwardly facing base and a distally facing surface, the latter in combination forming a distal sliding surface for the brake member 575. In combination the brake teeth form a radially oriented inwardly directed serrated surface structure.

The brake member 575 is in the form of a generally oval metal ring with a proximal (upper in FIG. 10B) sliding surface and an opposed distal sliding surface. On the distal surface is arranged a pair of radially oriented opposed guide portions 576 adapted to be arranged in the radial grooves 547 of the but housing. As the width of the brake member corresponding to the opposed guide portions is smaller than the inner diameter of the nut housing, the mounted brake member can slide back and forth corresponding to the guide grooves but cannot rotate. On the proximal surface and corresponding to the guide portions are arranged a pair of opposed brake protrusions 577 each having a general triangular configuration with an outwardly facing point, neighbouring first and second inclined surfaces (one of which serves as a brake surface 578) and an inwardly facing base. The brake protrusions are adapted to be received in the spaces between the teeth structures on the outer drive member. The brake member is further provided with a second set of proximally-facing opposed protrusions being offset 90 degrees relative to the brake protrusions and located corresponding to the inner edge of the oval ring, these protrusions merely adding stiffness and weight to the brake member.

In an assembled state the brake member 575 is mounted between the nut housing 540 and the outer drive member 550 with a slight axial play providing that mainly gravity will result in sliding contact between distal and proximal surfaces of the members, i.e. with the pen-formed drug delivery device positioned vertically either the distal sliding surface of the brake member will slide on the flange proximal surface 547 or the proximal sliding surface of the brake member will slide on the distal sliding surfaces of the sliding surface of the brake member will slide on the flange proximal surface 558. The distal surfaces of the brake member guide portions and the proximal surfaces of the brake protrusions are not in sliding contact with the guide grooves respectively the outer drive member distal surface.

The braking mechanism of FIGS. 10A and 10B works as follows: When the drive mechanism rotates driven by the released spring the outer drive member with the circumferentially arranged brake teeth rotates as well being part of the mechanism. For a brake protrusion positioned next to a brake tooth the contacting surface of the "leading" brake tooth will generate a tangential force on the brake member's contacting brake surface, and the nut housing will generate a corresponding reaction force on the opposite surface of the opposed guide portion. As the brake surface on the rotating part of the drive mechanism is inclined relative to a radial line towards the axis of revolution of the rotating part, and the contacting surface of the guide groove on the nut housing is parallel with a radial line towards the axis of revolution of the rotating part, the tangential force on the brake protrusion will result in radial movement of the brake member towards the centre axis corresponding to the guide grooves.

At some time the sliding brake surface on the brake member will lose contact with the brake surface on the rotating part because the tooth on the rotating part has limited length. However, after a short movement with no contact between the brake member 575 and the rotating part the opposed brake projection on the brake member will hit an inclined surface on a brake tooth on the opposite side of the rotating drive member 550. Subsequently the rotating part will force the brake member to change direction and slide back in the opposite direction. This movement of the brake member back and forth will continue until the drive mechanism has stopped.

Because the brake member has a finite mass, it requires a certain force to make it accelerate and change direction of velocity. During normal operation of the device, when the drive mechanism rotates slowly, i.e. due to flow resistance of the drug being expelled through a narrow needle, the acceleration of the brake member is small and requires only little force. But when the drive mechanism rotates fast the braking effect is high due to brake member inertia as well as friction and impact generated heating of the components.

With no contact between the cartridge piston and piston rod, and with no other elements preventing the motion, the drive mechanism will continue to spin up until the force required to accelerate the brake member back and forth equals the force from the spring. The kinetic energy from the spring is lost in the brake due to acceleration of the brake member, sliding friction when the brake member slides between the rotating outer drive member and the nut housing, and to internal friction in the material when the brake member impacts on an opposing sliding surface and stops/changes direction of motion.

The amount of energy that is used to perform the linear movement of the brake member depends on the speed and the weight of the brake member (kinetic energy=$\frac{1}{2}mv^2$). In the described embodiment the brake member 575 is formed from a polymer but could alternatively be formed from metal. Since the speed of the brake member is defined by the rotational speed of the drive mechanism and the angles of the inclined sliding surfaces, the amount of energy used for moving the brake member will increase when the rotational speed of the drive mechanism increases.

As described above the brake member generates a braking effect due to its inertia and due to friction and impact generated heating of the components. All these braking effects increase when the speed of the drive mechanism is high. Therefore the braking effect from the braking element will be much higher when there is no contact between the piston rod washer and the cartridge piston.

Figure 11A:
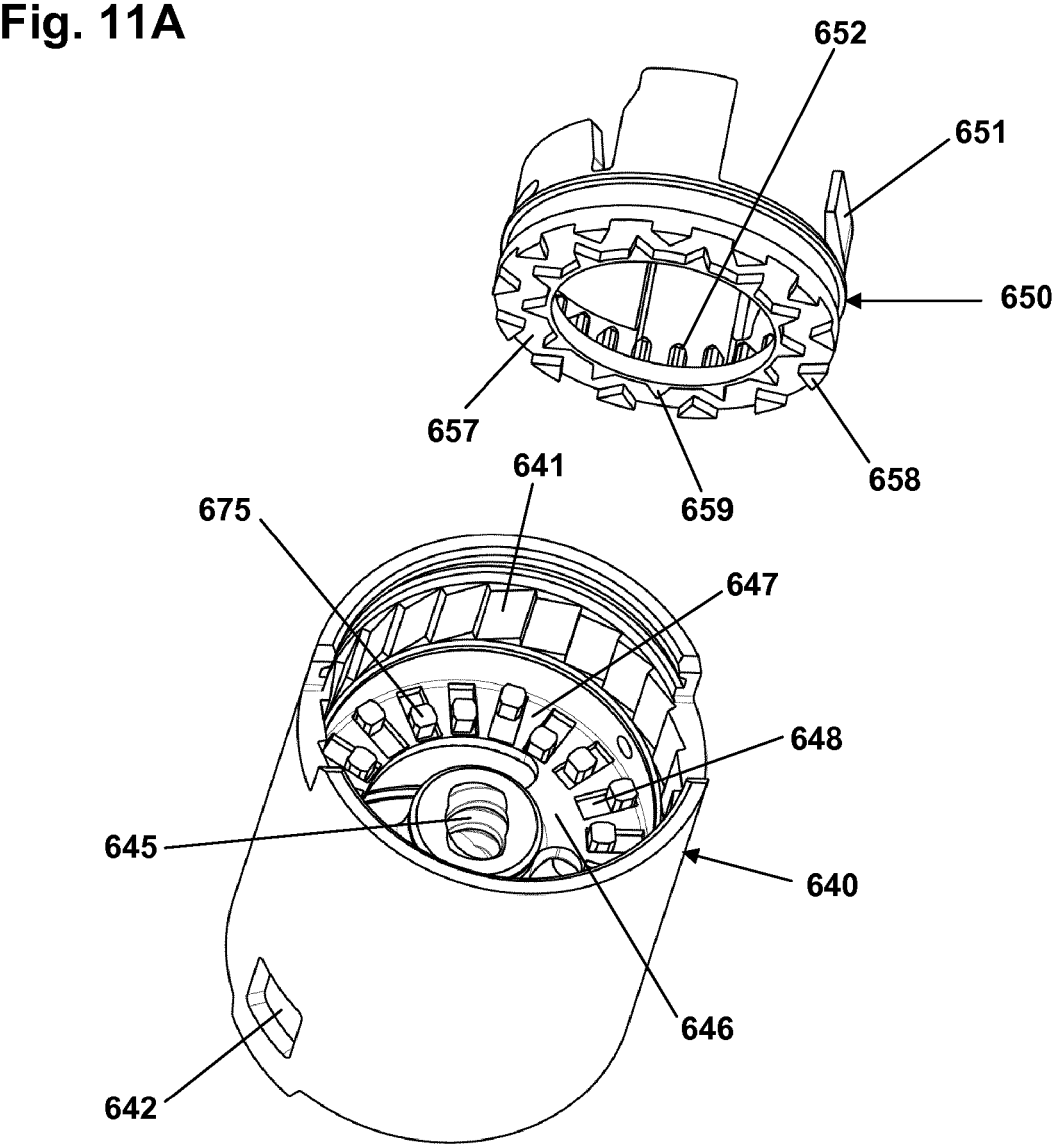
FIGS. 11A and 11B show components for a further rotational brake for an expelling mechanism.
Figure 11B:
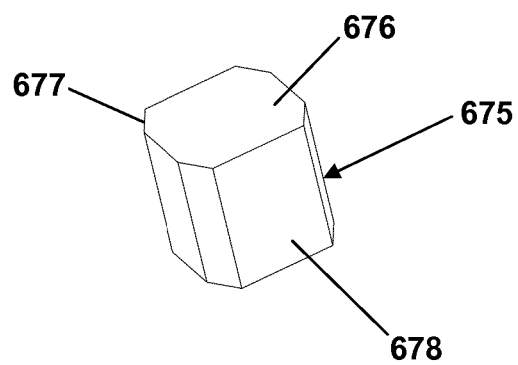

With reference to FIGS. 11A and 11B an alternative configuration of the brake assembly of FIGS. 10A and 10B will be described, the main difference being the incorporation of a plurality of relatively small metal brake members 675 instead of a single relatively large brake member.

More specifically, the nut housing 640 comprises as the FIG. 10A embodiment a central nut portion with a threaded bore 645 being carried in the nut housing by supporting arm structures 646, circumferentially arranged ratchet teeth 641 on the nut housing inner surface, a circumferential flange with a proximal surface 647 and distal guide openings 642. However, instead of only two guide grooves in the FIG. 10A nut housing a plurality of radial guide grooves 648 are formed in the flange proximal surface, each guide groove comprising opposed radial surfaces, one serving as a brake surface. The outer drive member 650 comprises as the FIG. 10A embodiment a pair of ratchet arms 651, a plurality of circumferentially arranged coupling teeth 652 and a distally facing circumferential sliding surface 657 with a plurality of peripherally arranged outer brake teeth structures 658. Further, a plurality of circumferentially arranged inner brake teeth structures 659 is provided, each brake tooth having a general triangular configuration corresponding to the outer brake teeth but with an outwards facing point, the inner teeth being arranged off-set relative to the outer teeth corresponding to the spacing between the latter. In combination the outer brake teeth form a radially oriented inwardly directed serrated surface structure and the inner brake teeth form a radially oriented outwardly directed serrated surface structure.

Each brake member 675 has a general cube form with four side surfaces, one of which serves as a brake surface 578, a proximal (upper in FIG. 11B) sliding surface 676 and an opposed distal sliding surface. The four "corners" arranged perpendicular to the sliding surfaces are in the form of four inclined chamfers, two of which serve as brake chamfers 677 adapted to engage the brake surfaces of a brake teeth.

In an assembled state the brake members 675 are mounted between the nut housing 640 and the outer drive member 650, each brake member being arranged in a corresponding guide groove 648 with a slight axial play providing that mainly gravity will result in sliding contact between distal and proximal surfaces of the members, i.e. with the pen-formed drug delivery device positioned vertically either the distal sliding surface of the brake member will slide on the proximal guide groove bottom surface or the proximal sliding surface 676 of the brake member will slide on the distal sliding surface 657 of the outer drive member. In the shown embodiment the opposed flange surfaces 657, 647 are arranged perpendicularly to the axis of rotation, however, alternatively they could be inclined, i.e. having a generally concave or convex configuration. Correspondingly, the orientation of the guide grooves could deviate from the shown strict radial orientation.

The braking mechanism of FIGS. 11A and 11B works as follows: When the drive mechanism rotates driven by the released spring the outer drive member will generate tangential forces on the brake chamfers on a number of the brake members, and the nut housing guide grooves will generate corresponding reaction forces on the opposed brake surface on the brake member. As the sliding brake surfaces on the outer drive member are inclined relative to radial lines towards the axis of revolution of the outer drive member, and the guide groove brake surfaces on the nut housing are parallel with radial lines towards the axis of revolution of the outer drive member, the tangential forces on the brake members will result in radial movement of the brake members (some of the brake members will move towards the centre axis and some will move away from the centre axis). Hereby the brake members slide on their brake chamfers 677 towards the outer drive member and on their brake surfaces 678 towards the nut housing.

At some time the brake chamfer on a given brake member will lose contact to the sliding surface (e.g. on the set of teeth on the outer circumference on the outer drive member), because the tooth brake surface on the outer drive member has limited length. However, after a short movement with no contact between the brake member and the outer drive member, the other side on the brake member will hit the sliding surface on the tooth on the opposite set of teeth of the outer drive member (e.g. on the set of teeth on the inner circumference on the outer drive member). Subsequently the outer drive member will force the brake members to change direction and slide in the opposed direction. This movement of the brake members will continue until the drive mechanism is stopped.

During the above-described operation of the braking mechanism as shown in FIGS. 11A and 11B essentially the same braking effects as was described above in respect of the braking mechanism as shown in FIGS. 10A and 10B will take place, the main difference being that a plurality of smaller brake elements are moved radially back and forth instead of a single larger brake element.

In the embodiments of FIGS. 10A and 10B the one or more brake elements are arranged non-rotational relative to the housing, however, alternatively the brake element(s) may rotate with the rotating component, the serrated surface structure being arranged on the housing and the guide structures being arranged on the rotating component.

As described above the scale drum 140 is in rotational threaded engagement with the inner surface of the inner proximal housing 201 via cooperating thread structures 142, 202. Whereas the proximal housing in the shown embodiment comprises a female thread in the form of an essentially complete helical groove 220, the scale drum is merely provided with a male thread in the form of a thread structure arranged corresponding to the proximal end portion of the scale drum. The scale drum thread structure could be in the form of a single flange structure spanning e.g. 360 degrees or be divided into a number of discrete flange portions or projections, i.e. "groove guides", engaging the helical groove. By arranging the scale drum outer thread structure at the end(s) only instead of circumferentially along the entire length of the drum it is possible to print the helically arranged rows of dose numerals closer to each other thereby allowing a shorter drum length for a given number of numerals.

Having described the different components of the expelling mechanism and their functional relationship as well as the operation of the cartridge holder and coupling, operation of the pen expelling mechanism will be described next with reference mainly to FIGS. 3 and 4.

The pen mechanism can be considered as two interacting systems, a dose system and a dial system. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 280, the actual displacement of the piston being performed by the piston rod. During dose delivery, the piston rod is rotated by the inner drive member 270 and due to the threaded interaction with the threaded nut bore 245 which is fixed to the housing, the piston rod moves forward in the distal direction. Between the rubber piston and the piston rod, the piston washer 289 is placed which serves as a bearing for the rotating piston rod and evens out the pressure on the rubber piston. As the piston rod has a non-circular cross section where the piston rod drive member engages with the piston rod, the inner drive member is locked rotationally to the piston rod, but free to move along the piston rod axis. Consequently, rotation of the inner drive member results in a linear forwards (i.e. distal) movement of the piston. The outer drive member 250 is provided with a pair of ratchet arms 251 which, via the coupling member 260, prevent the inner drive member from rotating clockwise (seen from the push button end). Due to the engagement with the inner drive member, the piston rod can thus only move forwards. During dose delivery, the inner drive member rotates anti-clockwise and the ratchet arms 251 provide the user with small clicks due to the engagement with the ratchet teeth on the nut housing inner surface, e.g. one click per unit of insulin expelled.

Turning to the dial system, the dose is set and reset by turning the dial member 170. When turning the dial member, the reset tube 130, the EOC member 285, the ratchet tube 120, the ratchet member 110 and the scale drum 140 all turn with it. As the ratchet tube is connected to the distal end of the torque spring 139 via the ratchet member, the spring is loaded. During dose setting, the arm 111 of the ratchet performs a dial click for each unit dialled due to the interaction with the inner teeth structure 291 of the clutch member 290. In the shown embodiment the clutch member is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 343.

The ratchet 110, 291 between the ratchet tube 120 and the clutch member 290 prevents the spring from turning back the parts. During resetting, the reset tube moves the ratchet arm 111, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 291 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

To deliver a set dose, the push button 181 is pushed in the distal direction by the user. The reset tube 130 decouples from the dial member as the toothed engagement 162, 172 between the dial member and the button module is moved axially apart (see below) and subsequently the clutch member 290 disengages the housing splines 204 and starts to rotate together with the outer drive member 270. Now the dial mechanism returns to "zero" together with the clutch member, the drive members 250, 270 and the coupling member 260, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 285 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction by the spring, i.e. the now set dose corresponds to the remaining drug content in the cartridge.

The scale drum 140 is provided with a distal stop surface adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 100 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism. This said, the dial member may be provided with a torque limiter allowing it to be dialled past its normal stop position, see below.

To prevent accidental over-dosage in case something should fail in the dialling mechanism allowing the scale drum or the ratchet tube to move beyond their zero-position, the EOC member serves to provide a security system. More specifically, in an initial state with a full cartridge the EOC member is positioned in a distal-most axial position almost in contact with the inner drive element. After a given dose has been expelled the EOC member will again be positioned almost in contact with the inner drive element. Correspondingly, the EOC member will lock against the inner drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm on the spring base is forced backwards by the progressing scale drum. Just before "zero" the arm is released and the arm hits a surface on the scale drum.

The shown mechanism is further provided with a torque limiter in order to protect the mechanism from overload applied by the user via the dial member. This feature is provided by the interface between the dial member 170 and the button module 160 which as described above are rotationally locked to each other during dose setting. More specifically, in the shown embodiment the dial member is provided with a circumferential inner teeth structure 172 engaging a number of corresponding teeth arranged on a flexible carrier portion 162 of the button module. The button module teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth, this being the case for rotation in both directions.

With reference to FIGS. 4-6 the combined actuation mechanism for the cartridge holder and the drive coupling was described. Next with reference to FIGS. 12 and 13 an alternative cartridge holder mechanism will be described, the mechanism comprising blocking means configured to prevent the cartridge holder from being actuated between the closed and the open state when a cartridge 780 with a mounted needle assembly 790 is held in a mounted position as shown in FIG. 12A.

With reference to FIG. 4 a unitary cartridge holder 330 was described, comprising a pair of opposed lateral control protrusions 333 guided in a control track providing controlled axial movement of the cartridge holder when rotated relative to the track by means of the user rotating the actuation sleeve. Indeed, each control protrusion and the associated portion of the control track provide the same movement.

Figure 12A:
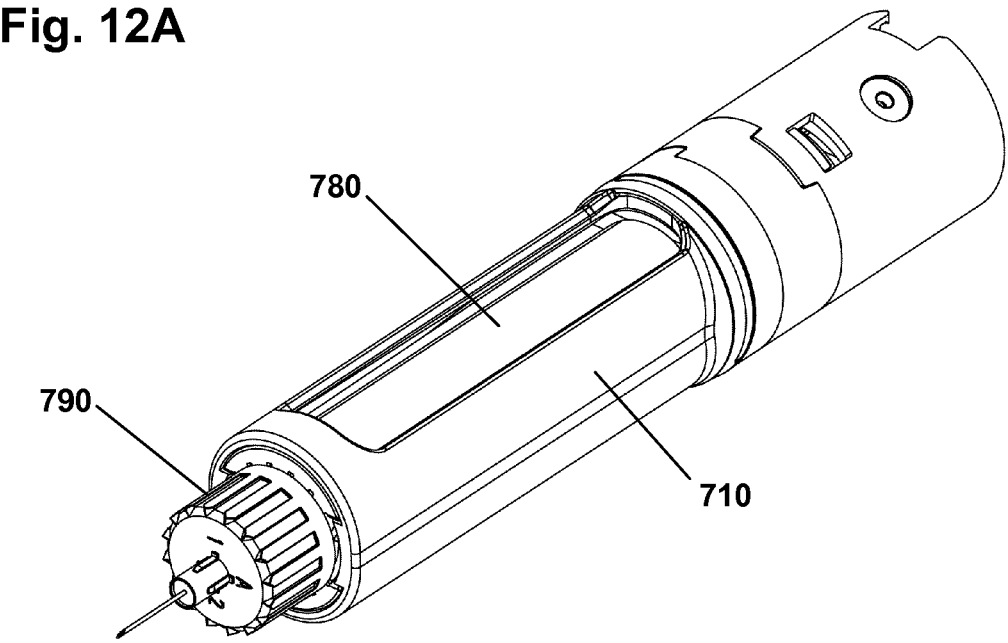
FIGS. 12A and 12B show an alternative configuration for a front-loaded cartridge holder with and without a cartridge and needle assembly mounted.
Figure 12B:
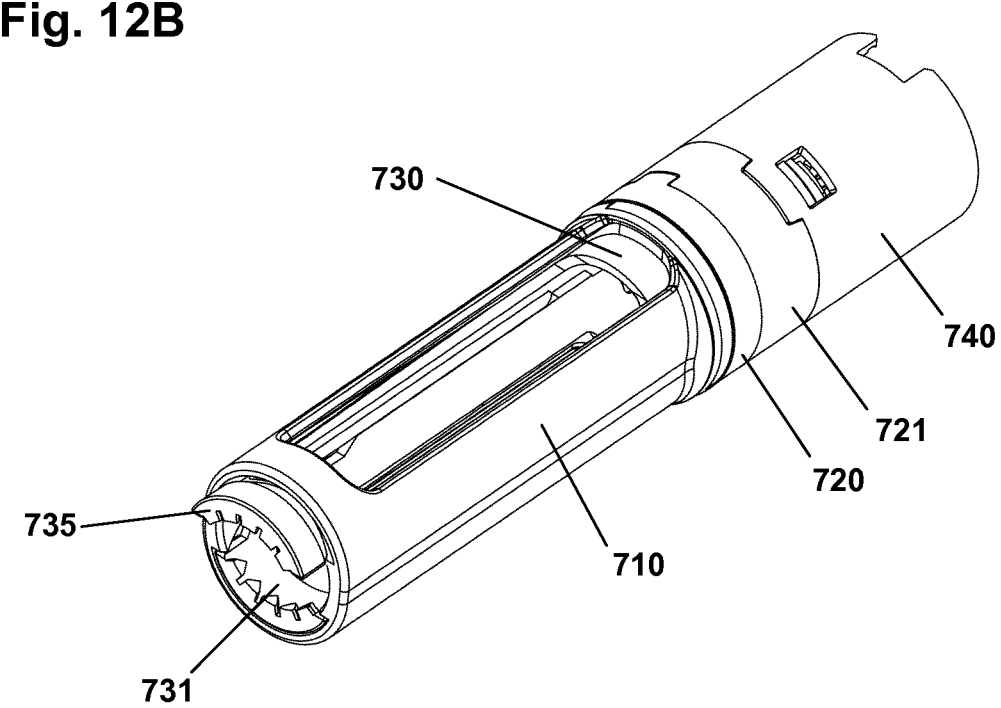

In contrast, in the embodiment of FIGS. 12A and 12B the cartridge holder has been divided lengthwise providing first and second cartridge holder members 730, 731, the axial movement of each member being controlled independently by a control protrusion arranged in an associated portion of a control track formed by the sleeve mount 720 and the distal housing 721 in combination, the latter mounted to nut housing 740.

Whereas the control protrusions on the two cartridge holder members may be identical, the corresponding two control track portions are different providing that the two cartridge holder parts can move axially independently of each other as the actuation sleeve 710 is rotated, this as shown in FIG. 12B in which only the gripping jaw 735 of the first cartridge holder member has been moved distally.

Figure 13A:
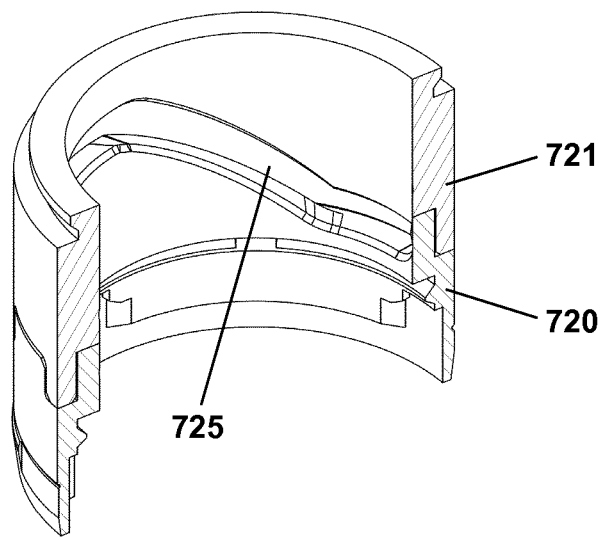
FIGS. 13A and 13B show control tracks for the cartridge holder of FIG. 12B.

Turning to FIG. 13A the first control track portion 725 that controls the first cartridge holder member is designed with a first slope arranged to ensure that the first cartridge holder member moves relatively far distally during the first part of the rotation from the operational state towards the loading state.

Figure 13B:
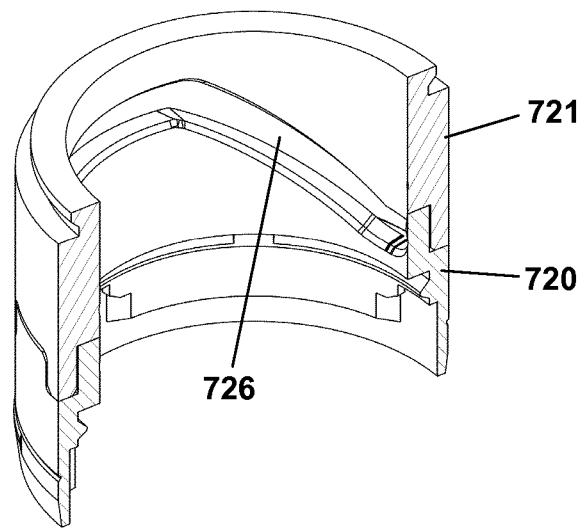

Turning to FIG. 13B the second control track portion 726 that controls the second cartridge holder member is designed with a second slope arranged to ensure that the second cartridge holder member does not move distally during the first part of the rotation of the actuation sleeve from the operational state towards the loading state. This second cartridge holder member with its gripping jaw will therefore hold a loaded cartridge in the operational position during the first part of the rotation, this corresponding to the above-described embodiment. In FIG. 13B it can also be seen that the second slope on the guiding track starts "later" as compared to the first slope when the control protrusions on the two cartridge holder members (in the figures) are moved from left to right.

In a situation of use and with a loaded cartridge, both of the cartridge holder members are in their proximal-most position corresponding to an operational state, see FIG. 1A showing a cartridge held in a loaded position. When a needle assembly is mounted on the needle hub mount 95 of the cartridge, the proximal portion of the needle hub is positioned in close proximity to the distal-most portion of the gripping jaws. Turning to FIG. 12B showing a cartridge holder with no cartridge inserted, the actuation sleeve 710 has been rotated an amount resulting in the second cartridge holder member having been moved distally whereas the first cartridge holder member essentially has not been moved axially. Further rotation would then result in also the first cartridge holder member being moved distally, i.e. corresponding to FIG. 1B. However, in case a needle assembly had been mounted on the cartridge hub mount the gripping jaw of the second cartridge holder member would engage the proximal-most edge of the needle hub, this preventing further rotation of the actuation sleeve due to the control protrusion of the second cartridge holder member arranged in the second control track portion blocking further rotation. By this arrangement the second cartridge holder member serves as a blocking member preventing the cartridge holding means from being actuated between the closed and the open state.

In an alternative embodiment (not shown), the blocking means could comprise a blocking member adapted to be moved to a blocking position when a needle assembly is mounted on a mounted cartridge, e.g. a rod member guided axially inside the actuation sleeve and serving to block the actuation sleeve when pushed proximally. This type of blocking means actuated when a needle assembly is attached could be considered as "active" in contrast to "passive" where the blocking means is prevented from moving due to a mounted needle assembly as in the embodiment shown in FIGS. 12A and 12B.

With reference to FIGS. 10 and 11 two versions of a brake assembly was described. As an alternative to a brake mechanism in a spring-driven drug delivery device in which the problem of undesired high speeds of components is an issue, an energy absorbing end-of-dose stop may be provided adapted to absorb and dissipate energy from an impact.

An end of dose stop made by polymers will normally be elastic up to a certain threshold level of impact force. If the impact force is lower than the threshold level the end of dose stop will deform elastically, i.e. no yield. However if the energy at impact is high due to high speed, the end of dose stop will deform plastically, with a reaction force substantially equal to the threshold force level. Since the reaction force from the end of dose stop is limited to the threshold level it limits the forces on the other components in the device, i.e. parts of the housing and parts of the drive mechanism and possibly parts of a sensor system. However the end of dose stop has been damaged due to the plastic yielding and may break.

Alternatively, an end of dose stop made by elastic metals will normally be able to withstand the energy at impact from the drive mechanism, even if it hits the end of dose stop at high speed. However the energy from the drive mechanism will lead to high forces, which will be counteracted with an identical reaction force. This reaction force will be transmitted to other components in the device, i.e. parts of the housing and parts of the drive mechanism and possibly parts of a sensor system. Therefore such an end of dose stop with elastic metal may result in other components being damaged.

However, with an end of dose stop made by a pseudo elastic material, e.g. shape memory alloys such as nickel-titanium, it is possible to combine the benefits without having the drawbacks from the two solutions described above. Springs made by pseudo elastic metals are known to have a normal elastic behaviour up to a certain threshold force level. If the impact force is lower than the threshold level the end of dose stop will deform elastically like the polymer end of dose stop described above. However, if the energy at impact is high due to high speed, the end of dose stop will deform with a reaction force substantially equal to the threshold force level. However since the end of dose stop is pseudo elastic it will be able to spring back without damage, even after a large deformation of the stop, i.e. with no yield. Since the reaction force from the end of dose stop is limited to the threshold level it limits the forces on the other components in the device.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device comprising or being adapted to receive a cartridge, the cartridge comprising a cylindrical body portion, an axially displaceable piston, and a distal outlet portion, the drug delivery device comprising:
   a housing,
   an expelling assembly adapted to axially move the piston of a cartridge to thereby expel a dose of drug, comprising:
      a drive spring which in an energized state is adapted to drive the expelling assembly,
      a rotating component adapted to rotate relative to an axis of rotation during expelling of a dose of drug,
      a user actuated release structure for releasing the drive spring to thereby expel a dose of drug,
   the device further comprising a brake element being moveable in a plane perpendicular to the axis of rotation, the brake element being adapted to engage the rotating component such that during rotation thereof the brake element is moved back and forth by the rotating component, whereby the brake element provides a braking action on the rotating component,
   wherein the brake element(s) is/are arranged non-rotational relative to the housing.

2. A drug delivery device as in claim 1, comprising a generally oval-shaped brake element.

3. A drug delivery device as in claim 1, comprising a plurality of brake elements.

4. A drug delivery device as in claim 1, comprising a non-rotational guide structure adapted to engage the brake element(s) to thereby guide the brake element(s) corresponding to the back and forth movement.

5. A drug delivery device as in claim 4, wherein the guide structure is formed integrally with a portion of the housing.

6. A drug delivery device as in claim 1, wherein the brake element(s) are moved radially.

7. A drug delivery device as in claim 1, wherein the rotating component comprises an engagement structure for engaging the brake element(s) during rotation, the engagement structure comprising one or more radially oriented serrated surface structures.

8. A drug delivery device as in claim 1, wherein the brake element(s) is/are arranged non-rotational relative to the rotating component.

9. A drug delivery device as in claim 8, comprising a guide structure formed integrally with the rotating component and being adapted to engage the brake element(s) to thereby guide the brake element(s) corresponding to the back and forth movement.

10. A drug delivery device as in claim 8, wherein the brake element(s) are moved radially.

11. A drug delivery device as in claim 8, comprising a non-rotational engagement structure for engaging the brake element(s) during rotation, the engagement structure comprising one or more radially oriented serrated surface structures.

12. A drug delivery device as in claim 11, wherein the engagement structure is formed integrally with a portion of the housing.

13. A drug delivery device as in claim 1, wherein one or more of the brake elements is/are freely moveable within boundaries defined by surrounding structures.

14. A drug delivery device as in claim 1, wherein:
the expelling assembly comprises a piston rod adapted to engage and axially displace a piston in a cartridge in a distal direction to thereby expel a dose of drug from the cartridge, and
the rotating component is in the form of a drive member adapted to be rotated by the strained drive spring to thereby move the piston rod in the distal direction.

15. A drug delivery device comprising or being adapted to receive a cartridge, the cartridge comprising a cylindrical body portion, an axially displaceable piston, and a distal outlet portion, the drug delivery device comprising:
a housing,
an expelling assembly adapted to axially move the piston of a cartridge to thereby expel a dose of drug, comprising:
a drive spring which in an energized state is adapted to drive the expelling assembly,
a rotating component adapted to rotate relative to an axis of rotation during expelling of a dose of drug,
a user actuated release structure for releasing the drive spring to thereby expel a dose of drug,
the device further comprising a brake element being moveable in a plane perpendicular to the axis of rotation, the brake element being adapted to engage the rotating component such that during rotation thereof the brake element is moved back and forth by the rotating component, whereby the brake element provides a braking action on the rotating component,
wherein the rotating component comprises an engagement structure for engaging the brake element(s) during rotation, the engagement structure comprising one or more radially oriented serrated surface structures.

16. A drug delivery device as in claim 15, comprising a generally oval-shaped brake element.

17. A drug delivery device as in claim 15, comprising a plurality of brake elements.

18. A drug delivery device as in claim 15, wherein the brake element(s) is/are arranged non-rotational relative to the housing.

19. A drug delivery device as in claim 18, comprising a non-rotational guide structure adapted to engage the brake element(s) to thereby guide the brake element(s) corresponding to the back and forth movement.

20. A drug delivery device as in claim 19, wherein the guide structure is formed integrally with a portion of the housing.

21. A drug delivery device as in claim 15, wherein the brake element(s) are moved radially.

22. A drug delivery device as in claim 15, wherein the brake element(s) is/are arranged non-rotational relative to the rotating component.

23. A drug delivery device as in claim 22, comprising a guide structure formed integrally with the rotating component and being adapted to engage the brake element(s) to thereby guide the brake element(s) corresponding to the back and forth movement.

24. A drug delivery device as in claim 22, wherein the brake element(s) are moved radially.

25. A drug delivery device as in claim 22, comprising a non-rotational engagement structure for engaging the brake element(s) during rotation, the engagement structure comprising one or more radially oriented serrated surface structures.

26. A drug delivery device as in claim 25, wherein the engagement structure is formed integrally with a portion of the housing.

27. A drug delivery device as in claim 15, wherein one or more of the brake elements is/are freely moveable within boundaries defined by surrounding structures.

28. A drug delivery device as in claim 15, wherein:
the expelling assembly comprises a piston rod adapted to engage and axially displace a piston in a cartridge in a distal direction to thereby expel a dose of drug from the cartridge, and
the rotating component is in the form of a drive member adapted to be rotated by the strained drive spring to thereby move the piston rod in the distal direction.

* * * * *

UNITED STATES PATENT AND TRADEMARK OFFICE
CERTIFICATE OF CORRECTION

PATENT NO. : 10,213,559 B2
APPLICATION NO. : 15/028867
DATED : February 26, 2019
INVENTOR(S) : Soerensen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 313 days.

Signed and Sealed this
Twenty-ninth Day of October, 2019

Andrei Iancu
*Director of the United States Patent and Trademark Office*